US008318934B2

(12) United States Patent
Epa et al.

(10) Patent No.: US 8,318,934 B2
(45) Date of Patent: Nov. 27, 2012

(54) PROCESS FOR CHIRAL RESOLUTION OF 2-SUBSTITUTED 4-SUBSTITUTED 1,3-OXATHIOLANES

(75) Inventors: Widanagamage Ruwansiri Epa, Cragieburn (AU); Sebastian Mario Marcuccio, Endeavour Hills (AU); John Joseph Deadman, Carlton (AU)

(73) Assignee: Avexa Limited, Richmond (AU)

( * ) Notice: Subject to any disclaimer, the term of this patent is extended or adjusted under 35 U.S.C. 154(b) by 0 days.

(21) Appl. No.: 12/680,137

(22) PCT Filed: Sep. 26, 2008

(86) PCT No.: PCT/AU2008/001433
§ 371 (c)(1),
(2), (4) Date: Aug. 17, 2010

(87) PCT Pub. No.: WO2009/039582
PCT Pub. Date: Apr. 2, 2009

(65) Prior Publication Data
US 2010/0305321 A1  Dec. 2, 2010

Related U.S. Application Data

(60) Provisional application No. 60/981,252, filed on Oct. 19, 2007.

(30) Foreign Application Priority Data

Sep. 28, 2007 (AU) ................................. 2007905335

(51) Int. Cl.
*C07D 239/47* (2006.01)
(52) U.S. Cl. ....................................................... 544/317
(58) Field of Classification Search .................. None
See application file for complete search history.

(56) References Cited

U.S. PATENT DOCUMENTS
5,587,480 A * 12/1996 Belleau et al. ................ 544/310
2006/0199786 A1  9/2006 Cimpoia et al.

FOREIGN PATENT DOCUMENTS
WO  WO 2006/096954  9/2006

OTHER PUBLICATIONS

Jurgen Fuhrhop & Gustav Penzlin, Organic Synthesis: Concepts, Methods, Starting Materials, 216 (VCH Publishers, Inc. 1994) (1983).*
Brooks et al., The Separation of Steroid Alcohols by Chromatography of their Benzoates on Alumina, W. 12, Postgraduate Medical School, 212-217 (1952).*
International Search Report for Application No. PCT/AU2008/001433, dated Apr. 2, 2009.

* cited by examiner

*Primary Examiner* — Janet Andres
*Assistant Examiner* — Timothy R Rozof
(74) *Attorney, Agent, or Firm* — McCarter & English, LLP; Maria Laccotripe Zacharakis; A. Jacqueline Wizeman

(57) ABSTRACT

The present invention relates to a novel process for the chiral resolution of 2-substituted 4-substituted 1,3-oxathiolanes and derivatives thereof. The present invention also relates to novel 2-substituted 4-substituted 1,3-oxathiolanes derivatives.

42 Claims, No Drawings

PROCESS FOR CHIRAL RESOLUTION OF 2-SUBSTITUTED 4-SUBSTITUTED 1,3-OXATHIOLANES

RELATED APPLICATIONS

This application is a 35 U.S.C. §371 national stage filing of International Application No. PCT/AU2008/001433, filed Sep. 26, 2008, which is related and claims priority to U.S. Provisional Application Ser. No. 60/981,252, filed Oct. 19, 2007, and Australian Patent Application No. 2007905335, filed Sep. 28, 2007. The entire contents of each of these applications are explicitly incorporated herein by this reference.

FIELD OF THE INVENTION

The present invention relates to a novel process for the chiral resolution of 2-substituted 4-substituted 1,3-oxathiolanes and derivatives thereof of general formula (I):

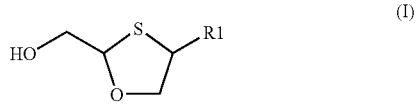

The present invention also relates to novel 2-substituted 4-substituted 1,3-oxathiolanes derivatives.

BACKGROUND

Classes of compounds known as 2-substituted 4-substituted 1,3-oxathiolanes, in particular derivatives of analogues of pyrimidine nucleosides have been found to have potent antiviral activity. In particular, these compounds have been found to act as potent inhibitors of HIV-1 replication in T-lymphocytes over a prolonged period of time with less cytotoxic side effects than compounds known in the art (see for example Belleau et. al. (1993) *Bioorg. Med. Chem. Lett.* Vol. 3, No. 8, 1723-1728). These compounds have also been found active against 3TC-resistant HIV strains (see for example Taylor et. al. (2000) *Antiviral Chem. Chemother.* Vol. 11, No. 4, 291-301; and Stoddart et. al. (2000) *Antimicrob. Agenst Chemother.* Vol. 44, No. 3, 783-786). These compounds are also useful in prophylaxis and treatment of hepatitis B virus infections. These compounds may be produced in accordance with the methods disclosed in WO 92/08717, WO 95/29176, WO 02/102796 and WO 2006/096954.

Compounds of the 2-substituted 4-substituted 1,3-oxathiolane family contain two chiral centres. Compounds that contain two chiral centres can exist as a mixture of four stereoisomers, where the configuration at the two chiral centres is (R,R) or (R,S) or (S,R) or (S,S). The (R,R) and (S,S) forms are known as cis enantiomers as they are non-superimposible mirror images of each other and the (R,S) and (S,R) forms are known as the trans enantiomers for the same reason. For human therapeutic use it is usually typically required to isolate the compound in only one of the stereoisomeric forms, also known as a chirally pure form. It can be that synthesis of a single stereoisomer can be achieved from a starting material with a single chiral centre in enantiomerically pure form or a suitable intermediate.

For example, cis-2-hydroxymethyl-4-(cytosin-1'-yl)-1,3-oxathiolane may be produced by the methods described by Mansour et al., "Anti-Human Immunodeficiency Virus and Anti-Hepatitis-B Virus Activities and Toxicities of the Enantiomers of 2'-Deoxy-3'-oxa-4'-thiacytidine and Their 5-Fluoro Analogues in vitro", *J. Med. Chem.*, (1995), Vol. 38, No. 1, 1-4, as well as the methods disclosed in U.S. Pat. No. 6,228,860, *Nucleosides and Nucleotides*, (1995) 14(3-5) 627-735 and Caputo et. al. in *Eur. j. Org. Chem.* (1999) Vol. 6, 1455-1458.

However methods of synthesis do not always form the new chiral centres stereospecifically, but instead give a ratio know as the enantiomeric excess (ee):

$$ee = \frac{[(\%\ desired\ isomer) - (\%\ opposite\ isomer)]}{sum(desired + opposite\ isomer)}$$

When compounds are desired as a single form, for example, if only the two (R, R) and (S, S)cis enantiomers are present, a single form being either the (R, R) or the (S, S) form, may be obtained by resolution of the mixture of the two cis enantiomers by chiral HPLC. A review of this technology may be found in "Enantiomers, Racemates and Resolutions" by J. Jacques, A. Collet & S. H. Wilen (John Wiley & Sons, 1981).

Alternatively, compounds or any convenient intermediate may be resolved by enzyme mediated enantioselective catabolism with a suitable enzyme such as cytidine deaminase or selective enzymatic degradation of a suitable derivative (see for example Storer et. al., "The resolution and Absolute Stereochemistry of the Enantiomers of cis 1[2 (Hydroxymethyl)-1,3-Oxathiolan-5-Yl)Cytosine (BCH-189): Equipotent Anti-HIV Agents", *Nucleosides & Nucleotides*, (1993) 12(2), 225-236).

The reaction of a racemic mixture of a compound with an optically active resolving acid or base can also be used for the enantiomeric resolution of the compound. For example, WO 2006/096954 discloses a method for the preparation of optically active cis 1,3-oxathiolanes. The method involves, (a) reacting a 1,3-oxathiolane compound in the cis configuration with a chiral acid to produce two diastereomeric salts; (b) recovering one of the two diastereomeric salts; and (c) desalting to remove the chiral acid. Preferred chiral acids include (+)-L-tartaric acid, (1R)-(−)-10-camphorsulfonic acid, (−)-2, 3-dibenzoyl-tartaric acid or (−)-L-malic acid. The method also discloses the addition of an achiral acid together with the chiral acid to produce the two diastereomeric salts. A disadvantage with the method of WO 2006/096954 however, is the salt formation step. This step requires the use of chiral acid reagents and in some cases also achiral acids. The salt formation step also requires the introduction of a further desalting step to obtain the desired optically active cis product.

The use of additional reagents, such as chiral acids, and extra steps in a process, such as the desalting step required in the method of WO 2006/096954, are undesirable in a commercial setting as they add to production costs as well as increase the production time of the desired product. Furthermore, with each additional step in a process, there is the potential for inefficient recovery of the final end product due to losses occurring with each step of the process.

The present inventors have found that by the correct choice of groups R2, R3 and R4, an optically active compound of general formula (II) or (III) may be obtained by selective recrystallisation. The present inventors have also found that the recrystallisation solvent of choice is selected on the basis of groups R2, R3 and R4. The present invention avoids the salting and desalting steps required by previous methods and provides a simpler, more efficient process to produce optically active cis 1,3-oxathiolanes. In a particularly preferred aspect the invention provides a way of separating an undesired diastereomer such as the trans diastereomer and enhancing the optical purity of the cis isomer by recrystallisation. The present invention also provides novel 2-substituted 4-substituted 1,3-oxathiolane derivatives.

SUMMARY OF THE INVENTION

According to a first aspect, the present invention provides a process for producing a compound of general formula (II) comprising the steps of:

(a) forming a 2-substituted 4-substituted 1,3-oxathiolane of general formula (II) or (III):

(II)

(III)

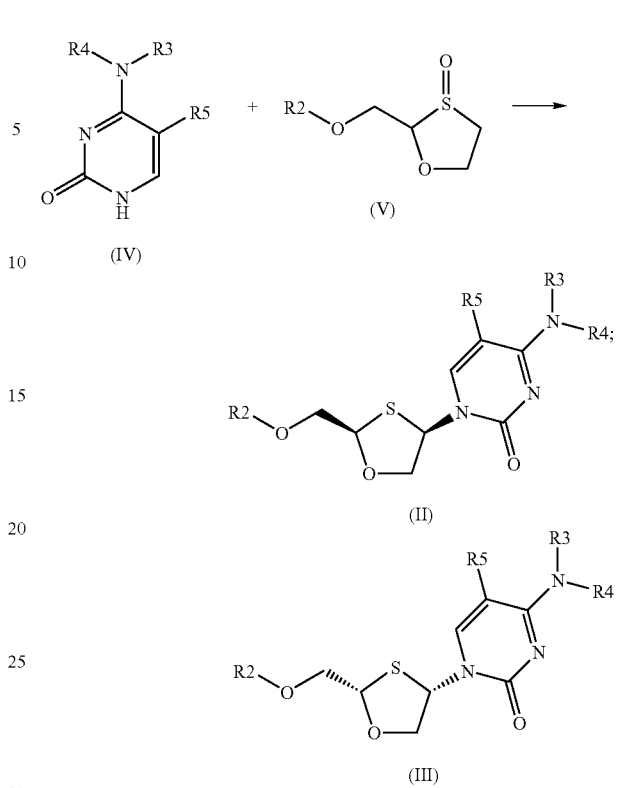

wherein
R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;

R3 and R4 are the same or different and are each individually selected from H or C(O)—R6;

R6 is C$_{6-12}$aryl or C$_{1-6}$alkylaryl in which the C$_{1-6}$alkylaryl is preferably C$_{1-6}$alkylC$_{6-12}$aryl; and R5 is H, Br, Cl, F, I or CF$_3$; and (b) selective recrystallisation of the compound of general formula (II) from a solvent wherein the solvent is C$_{1-6}$alcohol or mixtures of C$_{1-6}$alcohols.

In a particularly preferred embodiment, R6 is phenyl.

According to a second aspect, the present invention provides a process for producing a compound of general formula (II) comprising the steps of:

(a) reacting a base of general formula (IV) with a 1,3-oxathiolane of general formula (V) to produce a compound of general formula (II) or (III):

wherein
R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;

R3 and R4 are the same or different and are each individually selected from H or C(O)—R6;

R6 is C$_{6-12}$aryl or C$_{1-6}$alkylaryl in which the C$_{1-6}$alkylaryl is preferably C$_{1-6}$alkylC$_{6-12}$aryl; and R5 is H, Br, Cl, F, I or CF$_3$; and wherein the 1,3-oxathiolane of general formula (V) is the (R)-enantiomer in at least 60% ee; and (b) selective recrystallisation of the compound of general formula (II) from a solvent wherein the solvent is C$_{1-6}$alcohol or mixtures of C$_{1-6}$alcohols.

In a particularly preferred embodiment, R6 is phenyl.

According to a third aspect, the present invention provides a process for producing a compound of general formula (VI) comprising the steps of:

(a) forming a 2-substituted 4-substituted 1,3-oxathiolane of general formula (II) or (III):

(II)

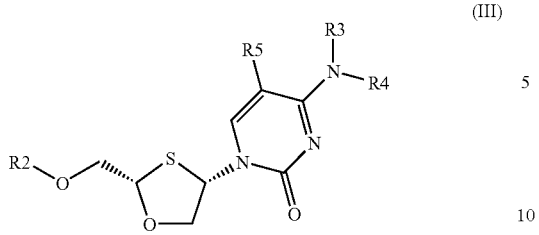

(III)

wherein

R2 is H, $C(O)C_{1-6}$alkyl, $C(O)OC_{1-6}$alkyl, $C(O)C_{6-12}$aryl, $C(O)OC_{6-12}$aryl, $C(O)C_{6-12}$arylalkyl, $C(O)OC_{6-12}$ arylalkyl, $C(O)C_{1-6}$alkylaryl, $C(O)OC_{1-6}$alkylaryl, or a silyl protecting group of general formula SiR7R8R9 wherein R7, R8 and R9 are each independently selected from $C_{1-6}$alkyl, aryl or $C_{1-6}$ alkylaryl;

R3 and R4 are the same or different and are each individually selected from H or C(O)—R6;

R6 is $C_{6-12}$aryl or $C_{1-6}$alkylaryl in which the $C_{1-6}$alkylaryl is preferably $C_{1-6}$alkyl$C_{6-12}$aryl; and R5 is H, Br, Cl, F, I or $CF_3$;

(b) selective recrystallisation of the compound of general formula (II) from a solvent wherein the solvent is $C_{1-6}$alcohol or mixtures of $C_{1-6}$alcohols; and (c) deprotecting the compound of general formula (II) to produce a compound of general formula (VI):

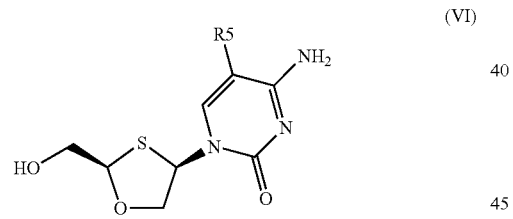

(VI)

In a particularly preferred embodiment, R6 is phenyl.

According to a fourth aspect, the present invention provides a process for producing a compound of general formula (VI) comprising the steps of:

(a) reacting a base of general formula (IV) with a 1,3-oxathiolane of general formula (V) to produce a compound of general formula (II) or (III):

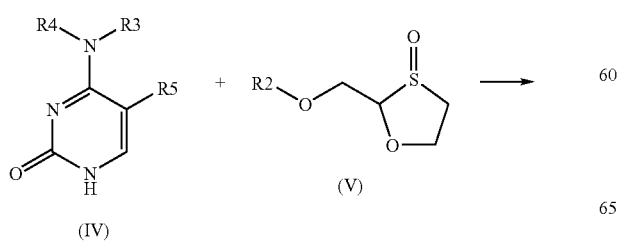

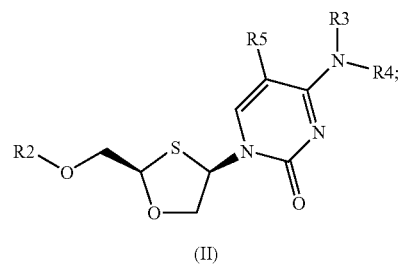

(II)

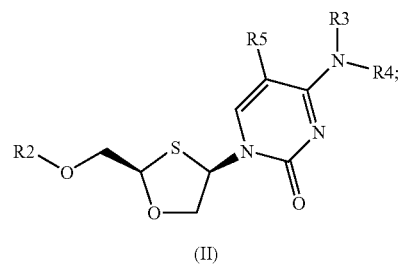

(III)

wherein

R2 is H, $C(O)C_{1-6}$alkyl, $C(O)O$—$C_{1-6}$alkyl, $C(O)C_{6-12}$aryl, $C(O)OC_{6-12}$aryl, $C(O)C_{6-12}$arylalkyl, $C(O)OC_{6-12}$ arylalkyl, $C(O)C_{1-6}$alkylaryl, $C(O)OC_{1-6}$alkylaryl, or a silyl protecting group of general formula SiR7R8R9 wherein R7, R8 and R9 are each independently selected from $C_{1-6}$alkyl, aryl or $C_{1-6}$ alkylaryl;

R3 and R4 are the same or different and are each individually selected from H or C(O)—R6;

R6 is $C_{6-12}$aryl or $C_{1-6}$alkylaryl in which the $C_{1-6}$alkylaryl is preferably $C_{1-6}$alkyl$C_{6-12}$aryl; and R5 is H, Br, Cl, F, I or $CF_3$; and wherein the 1,3-oxathiolane of general formula (V) is the (R)-enantiomer in at least 60% ee;

(b) selective recrystallisation of the compound of general formula (II) from a solvent wherein the solvent is $C_{1-6}$alcohol or mixtures of $C_{1-6}$alcohols; and (c) deprotecting the compound of general formula (II) to produce a compound of general formula (VI):

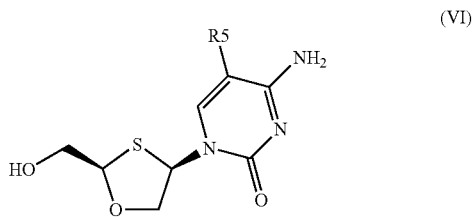

(VI)

In a particularly preferred embodiment, R6 is phenyl.

In a fifth aspect, the present invention provides a compound of general formula (VIII) or (IX):

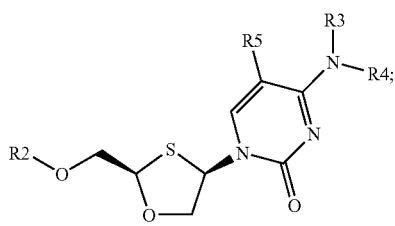

(VIII)

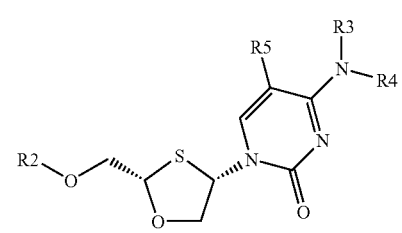

(IX)

wherein
- R2 is H, C(O)C$_{1-6}$alkyl, C(O)O—C$_{1-6}$alkyl, C(O)C$_{6-12}$aryl, C(O)OC$_{6-12}$aryl, C(O)C$_{6-12}$arylalkyl, C(O)OC$_{6-12}$arylalkyl, C(O)C$_{1-6}$alkylaryl, C(O)OC$_{1-6}$ alkylaryl, or a silyl protecting group of general formula SiR7R8R9 wherein R7, R8 and R9 are each independently selected from C$_{1-6}$alkyl, aryl or C$_{1-6}$ alkylaryl;
- R3 and R4 are each individually selected from H or benzoyl, provided that when R3 is H, R4 is not H and when R4 is H, R3 is not H; and
- R5 is H, Br, Cl, F, I or CF$_3$.

In a sixth aspect, the present invention provides a process for producing a compound of general formula (VI) or (VII) from a compound of general formula (VIII) or (IX) respectively, comprising the step of:

(a) deprotecting a compound of general formula (VIII) or (IX) to produce a compound of general formula (VI) or (VII) respectively:

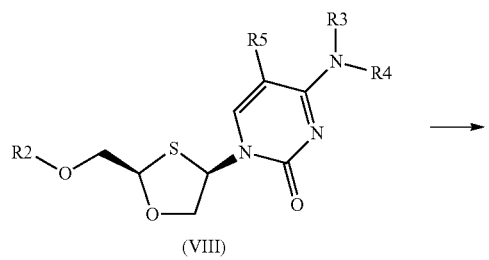

(VIII)

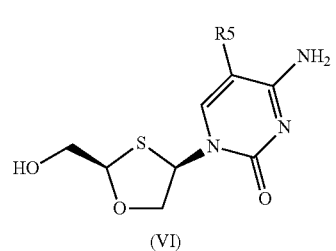

(VI)

-continued

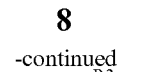

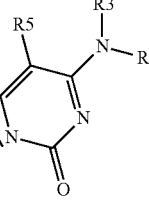

(IX)

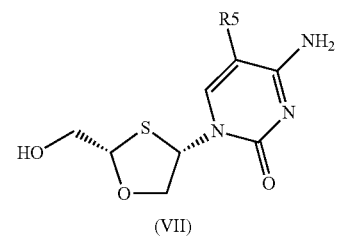

(VII)

wherein
- R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$arylalkyl, C(O)C$_{1-6}$alkylaryl, C(O)OC$_{1-6}$ alkylaryl, or a silyl protecting group of general formula SiR7R8R9 wherein R7, R8 and R9 are each independently selected from C$_{1-6}$alkyl, aryl or C$_{1-6}$ alkylaryl;
- R3 and R4 are each individually selected from H or benzoyl, provided that when R3 is H, R4 is not H and when R4 is H, R3 is not H; and
- R5 is H, Br, Cl, F, I or CF$_3$.

In accordance with a seventh aspect, the present invention provides a process for producing a compound of general formula (II) comprising the steps of:

(a) reacting a silylated base of general formula (X) with a 1,3-oxathiolane of general formula (V) to produce a compound of general formula (II) or (III):

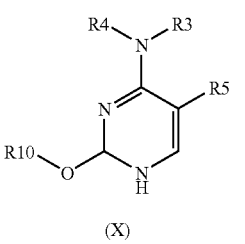

(X)

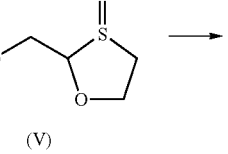

(V)

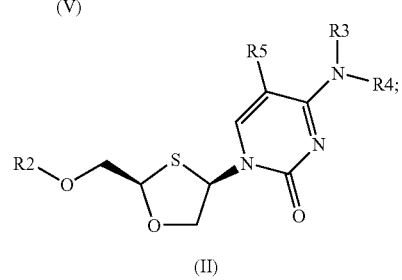

(II)

-continued

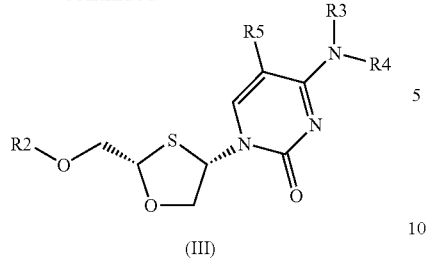

(III)

wherein

R2 is H, C(O)C$_{1-6}$alkyl, C(O)OC$_{1-6}$alkyl, C(O)C$_{6-12}$ aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;

R3 and R4 are the same or different and are each individually selected from H or C(O)—R6;

R6 is C$_{6-12}$aryl or C$_{1-6}$alkylaryl in which the C$_{1-6}$alkylaryl is preferably C$_{1-6}$alkylC$_{6-12}$aryl;

R5 is H, Br, Cl, F, I or CF$_3$; and

R10 is a silyl protecting group of general formula SiR7R8R9 as previously defined; and wherein the 1,3-oxathiolane of general formula (V) is the (R)-enantiomer in at least 60% ee; and (b) selective recrystallisation of the compound of general formula (II) from a solvent wherein the solvent is C$_{1-6}$alcohol or mixtures of C$_{1-6}$alcohols.

In a particularly preferred embodiment, R6 is phenyl.

In accordance with an eighth aspect, the present invention provides a process for producing a compound of general formula (VI) comprising the steps of:

(a) reacting a silylated base of general formula (X) with a 1,3-oxathiolane of general formula (V) to produce a compound of general formula (II) or (III):

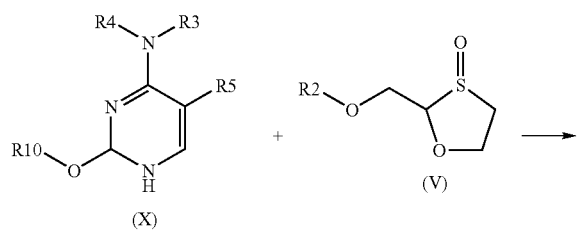

(X)      (V)

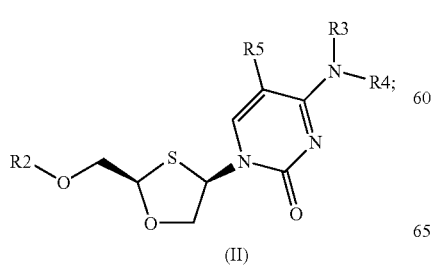

(II)

-continued

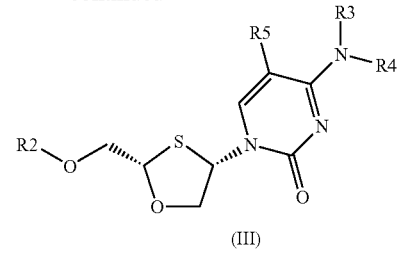

(III)

wherein

R2 is H, C(O)C$_{1-6}$alkyl, C(O)O—C$_{1-6}$alkyl, C(O)C$_{6-12}$ aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;

R3 and R4 are the same or different and are each individually selected from H or C(O)—R6;

R6 is C$_{6-12}$aryl or C$_{1-6}$alkylaryl in which the C$_{1-6}$alkylaryl is preferably C$_{1-6}$alkylC$_{6-12}$aryl; and R5 is H, Br, Cl, F, I or CF$_3$; and R10 is a silyl protecting group of general formula SiR7R8R9 as previously defined; and wherein the 1,3-oxathiolane of general formula (V) is the (R)-enantiomer in at least 60% ee;

(b) selective recrystallisation of the compound of general formula (II) from a solvent wherein the solvent is C$_{1-6}$alcohol or mixtures of C$_{1-6}$alcohols; and (c) deprotecting the compound of general formula (II) to produce a compound of general formula (VI):

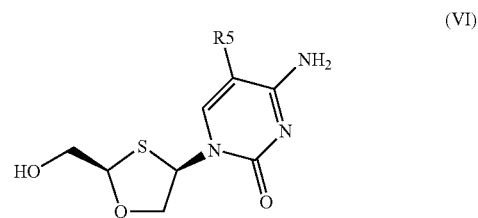

(VI)

In a particularly preferred embodiment, R6 is phenyl.

In accordance with a ninth aspect the present invention provides a compound of formula (XIII) and diastereomers thereof:

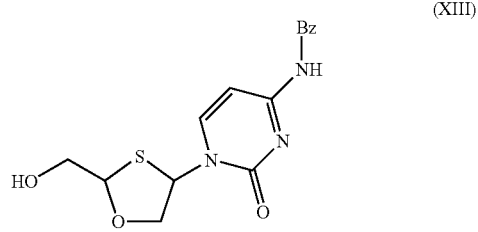

(XIII)

In accordance with a tenth aspect the present invention provides a process for separating a compound of general formula (II) from a compound of general formula (III) comprising the steps of:

(a) providing a mixture of 2-substituted 4-substituted 1,3-oxathiolanes of general formula (II) and (III):

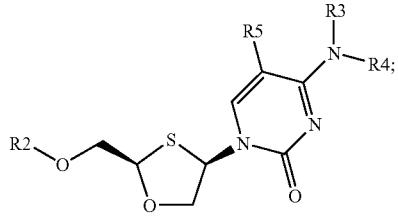
(II)

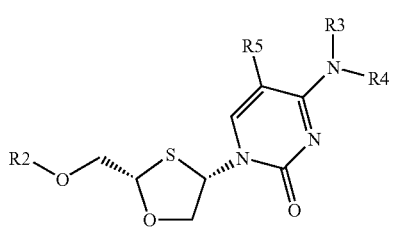
(III)

wherein

R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$ alkylaryl, or a silyl protecting group of general formula SiR7R8R9 wherein R7, R8 and R9 are each independently selected from C$_{1-6}$alkyl, aryl or C$_{1-6}$ alkylaryl;

R3 and R4 are the same or different and are each individually selected from H or C(O)—R6;

R6 is C$_{6-12}$aryl or C$_{1-6}$alkylaryl in which the C$_{1-6}$alkylaryl is preferably C$_{1-6}$alkylC$_{6-12}$aryl; and R5 is H, Br, Cl, F, I or CF$_3$; and (b) separating the compound of general formula (II) from the compound of general formula (III) by selective recrystallisation of the compound of general formula (II) from a solvent wherein the solvent is C$_{1-6}$alcohol or mixtures of C$_{1-6}$ alcohols.

In a particularly preferred embodiment, R6 is phenyl.

DETAILED DESCRIPTION OF THE PREFERRED EMBODIMENTS

The present invention will now be described without limitation by reference to the preferred embodiments.

The present invention advantageously provides a process for obtaining an optically active compound of general formula II or III by selective recrystallisation.

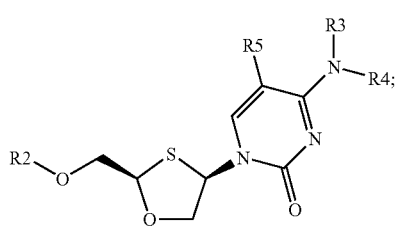
(II)

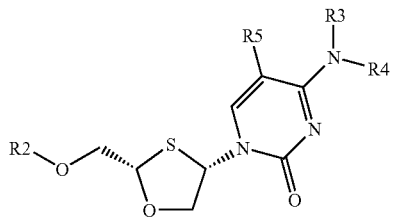
(III)

The compounds of general formula (II) or (III) may be selectively recrystallised from a mixture of the two cis isomers or a mixture of the four stereoisomers, these being the two cis isomers (II) and (III) and the two trans isomers (XI) and (XII) as follows:

Cis Isomers:

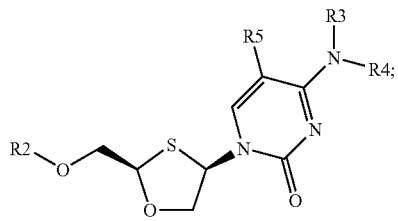
(II)

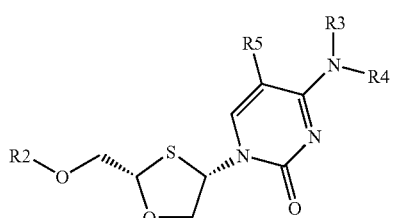
(III)

Trans Isomers:

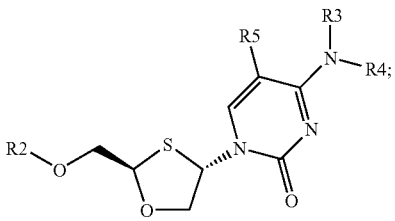
(XI)

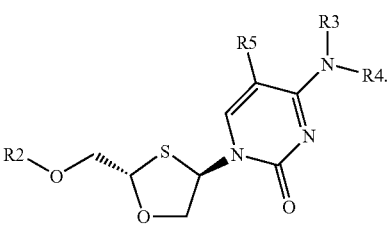
(XII)

According to a first aspect, the present invention provides a process for producing a compound of general formula (II) comprising the steps of:

(a) forming a 2-substituted 4-substituted 1,3-oxathiolane of general formula (II) or (III):

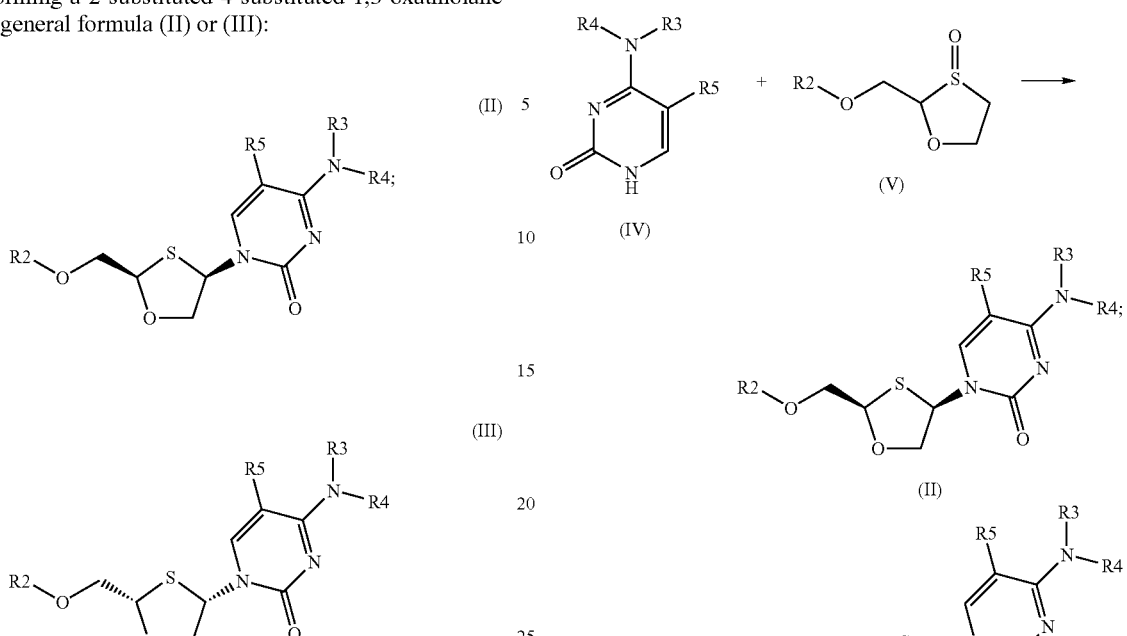

wherein

R2 is H, $C(O)C_{1-6}$alkyl, $C(O)OC_{1-6}$alkyl, $C(O)C_{6-12}$ aryl, $C(O)OC_{6-12}$aryl, $C(O)C_{6-12}$arylalkyl, $C(O)OC_{6-12}$ arylalkyl, $C(O)C_{1-6}$alkylaryl, $C(O)OC_{1-6}$ alkylaryl, or a silyl protecting group of general formula SiR7R8R9 wherein R7, R8 and R9 are each independently selected from $C_{1-6}$alkyl, aryl or $C_{1-6}$ alkylaryl;

R3 and R4 are the same or different and are each individually selected from H or C(O)—R6;

R6 is $C_{6-12}$aryl or $C_{1-6}$alkylaryl in which the $C_{1-6}$alkylaryl is preferably $C_{1-6}$alkyl$C_{6-12}$aryl; and R5 is H, Br, Cl, F, I or $CF_3$; and (b) selective recrystallisation of the compound of general formula (II) from a solvent wherein the solvent is $C_{1-6}$alcohol or mixtures of $C_{1-6}$alcohols.

In a particularly preferred embodiment, R6 is phenyl.

Preferably R2 is an acyl group, even more preferably a benzoyl group or an acetyl group.

Preferably R3 and R4 are each individually selected from H or benzoyl, provided that when R3 is H, R4 is not H and when R4 is H, R3 is not H.

Preferably R5 is H or F.

Preferably the silyl group of general formula SiR7R8R9 is selected from the group consisting of trimethylsilyl (TMS), tert-butyldiphenylsilyl (TBDPS), tert-butyldimethylsilyl (TBDMS/TBS), tri-iso-propylsilyl (TIPS) and triethylsilyl (TES).

According to a second aspect, the present invention provides a process for producing a compound of general formula (II) comprising the steps of:

(a) reacting a base of general formula (IV) with a 1,3-oxathiolane of general formula (V) to produce a compound of general formula (II) or (III):

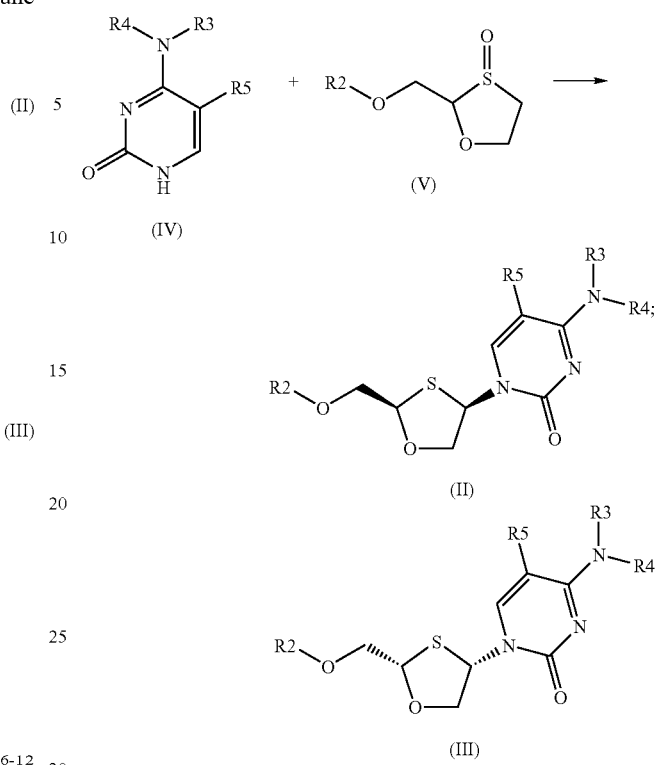

wherein

R2 is H, $C(O)C_{1-6}$alkyl, $C(O)OC_{1-6}$alkyl, $C(O)C_{6-12}$ aryl, $C(O)OC_{6-12}$aryl, $C(O)C_{6-12}$arylalkyl, $C(O)OC_{6-12}$arylalkyl, $C(O)C_{1-6}$alkylaryl, $C(O)OC_{1-6}$ alkylaryl, or a silyl protecting group of general formula SiR7R8R9 wherein R7, R8 and R9 are each independently selected from $C_{1-6}$alkyl, aryl or $C_{1-6}$ alkylaryl;

R3 and R4 are the same or different and are each individually selected from H or C(O)—R6;

R6 is $C_{6-12}$aryl or $C_{1-6}$alkylaryl in which the $C_{1-6}$alkylaryl is preferably $C_{1-6}$alkyl$C_{6-12}$aryl; and R5 is H, Br, Cl, F, I or $CF_3$; and wherein the 1,3-oxathiolane of general formula (V) is the (R)-enantiomer in at least 60% ee; and (b) selective recrystallisation of the compound of general formula (II) from a solvent wherein the solvent is $C_{1-6}$alcohol or mixtures of $C_{1-6}$alcohols.

In a particularly preferred embodiment, R6 is phenyl.

Preferably R2 is an acyl group, even more preferably a benzoyl group or an acetyl group.

Preferably R3 and R4 are each individually selected from H or benzoyl, provided that when R3 is H, R4 is not H and when R4 is H, R3 is not H.

Preferably R5 is H or F.

Preferably the silyl group of general formula SiR7R8R9 is selected from the group consisting of trimethylsilyl (TMS), tert-butyldiphenylsilyl (TBDPS), tert-butyldimethylsilyl (TBDMS/TBS), tri-iso-propylsilyl (TIPS) and triethylsilyl (TES).

According to a third aspect, the present invention provides a process for producing a compound of general formula (VI) comprising the steps of:

(a) forming a 2-substituted 4-substituted 1,3-oxathiolane of general formula (II) or (III):

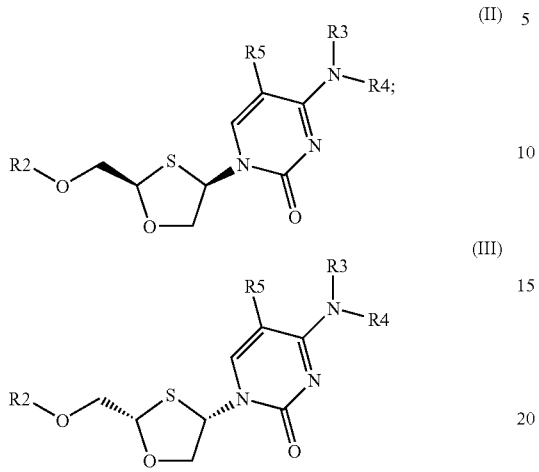

wherein
R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;
R3 and R4 are the same or different and are each individually selected from H or C(O)—R6;
R6 is C$_{6-12}$aryl or C$_{1-6}$alkylaryl in which the C$_{1-6}$alkylaryl is preferably C$_{1-6}$alkylC$_{6-12}$aryl; and
R5 is H, Br, Cl, F, I or CF$_3$;
(b) selective recrystallisation of the compound of general formula (II) from a solvent wherein the solvent is C$_{1-6}$alcohol or mixtures of C$_{1-6}$alcohols; and
(c) deprotecting the compound of general formula (II) to produce a compound of general formula (VI):

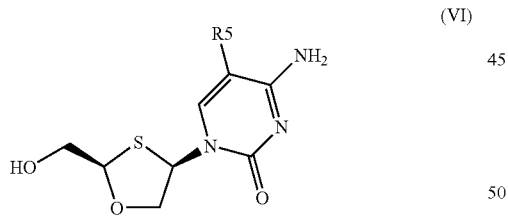

In a particularly preferred embodiment, R6 is phenyl.
Preferably R2 is an acyl group, even more preferably a benzoyl group or an acetyl group.
Preferably R3 and R4 are each individually selected from H or benzoyl, provided that when R3 is H, R4 is not H and when R4 is H, R3 is not H.
Preferably R5 is H or F.
Preferably the silyl group of general formula SiR7R8R9 is selected from the group consisting of trimethylsilyl (TMS), tert-butyldiphenylsilyl (TBDPS), tert-butyldimethylsilyl (TBDMS/TBS), tri-iso-propylsilyl (TIPS) and triethylsilyl (TES).
According to a fourth aspect, the present invention provides a process for producing a compound of general formula (VI) comprising the steps of:

(a) reacting a base of general formula (IV) with a 1,3-oxathiolane of general formula (V) to produce a compound of general formula (II) or (III):

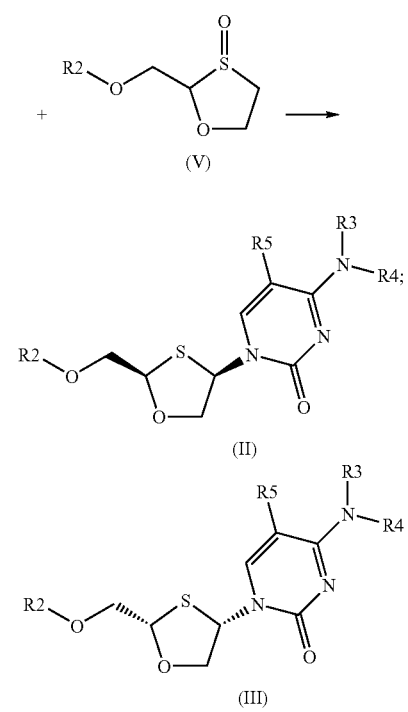

wherein
R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;
R3 and R4 are the same or different and are each individually selected from H or C(O)—R6;
R6 is C$_{6-12}$aryl or C$_{1-6}$alkylaryl in which the C$_{1-6}$alkylaryl is preferably C$_{1-6}$alkylC$_{6-12}$aryl; and
R5 is H, Br, Cl, F, I or CF$_3$; and
wherein the 1,3-oxathiolane of general formula (V) is the (R)-enantiomer in at least 60% ee;
(b) selective recrystallisation of the compound of general formula (II) from a solvent wherein the solvent is C$_{1-6}$alcohol or mixtures of C$_{1-6}$alcohols; and
(c) deprotecting the compound of general formula (II) to produce a compound of general formula (VI):

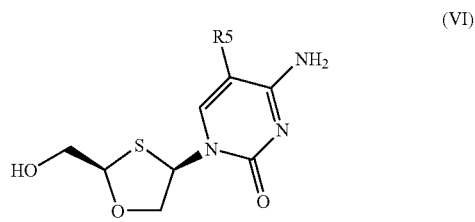

In a particularly preferred embodiment, R6 is phenyl.

Preferably R2 is an acyl group, even more preferably a benzoyl group or an acetyl group.

Preferably R3 and R4 are each individually selected from H or benzoyl, provided that when R3 is H, R4 is not H and when R4 is H, R3 is not H.

Preferably R5 is H or F.

Preferably the silyl group of general formula SiR7R8R9 is selected from the group consisting of trimethylsilyl (TMS), tert-butyldiphenylsilyl (TBDPS), tert-butyldimethylsilyl (TBDMS/TBS), tri-iso-propylsilyl (TIPS) and triethylsilyl (TES).

In a fifth aspect, the present invention provides a compound of general formula (VIII) or (IX):

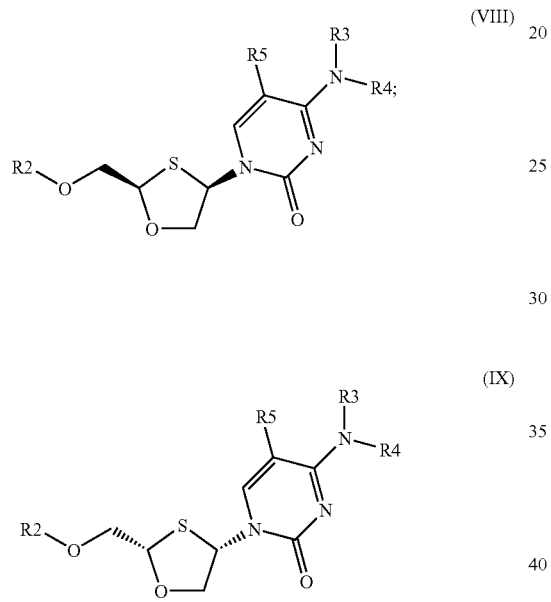

wherein

R2 is H, $C(O)C_{1-6}$alkyl, $C(O)OC_{1-6}$alkyl, $C(O)C_{6-12}$aryl, $C(O)OC_{6-12}$aryl, $C(O)C_{6-12}$arylalkyl, $C(O)OC_{6-12}$arylalkyl, $C(O)C_{1-6}$alkylaryl, $C(O)OC_{1-6}$ alkylaryl, or a silyl protecting group of general formula SiR7R8R9 wherein R7, R8 and R9 are each independently selected from $C_{1-6}$alkyl, aryl or $C_{1-6}$ alkylaryl;

R3 and R4 are each individually selected from H or benzoyl, provided that when R3 is H, R4 is not H and when R4 is H, R3 is not H; and R5 is H, Br, Cl, F, I or $CF_3$.

Preferably R2 is an acyl group, more preferably a benzoyl group or an acetyl group.

Preferably R5 is H or F.

In a sixth aspect, the present invention provides a process for producing a compound of general formula (VI) or (VII) from a compound of general formula (VIII) or (IX) respectively, comprising the step of:

(a) deprotecting a compound of general formula (VIII) or (IX) to produce a compound of general formula (VI) or (VII) respectively:

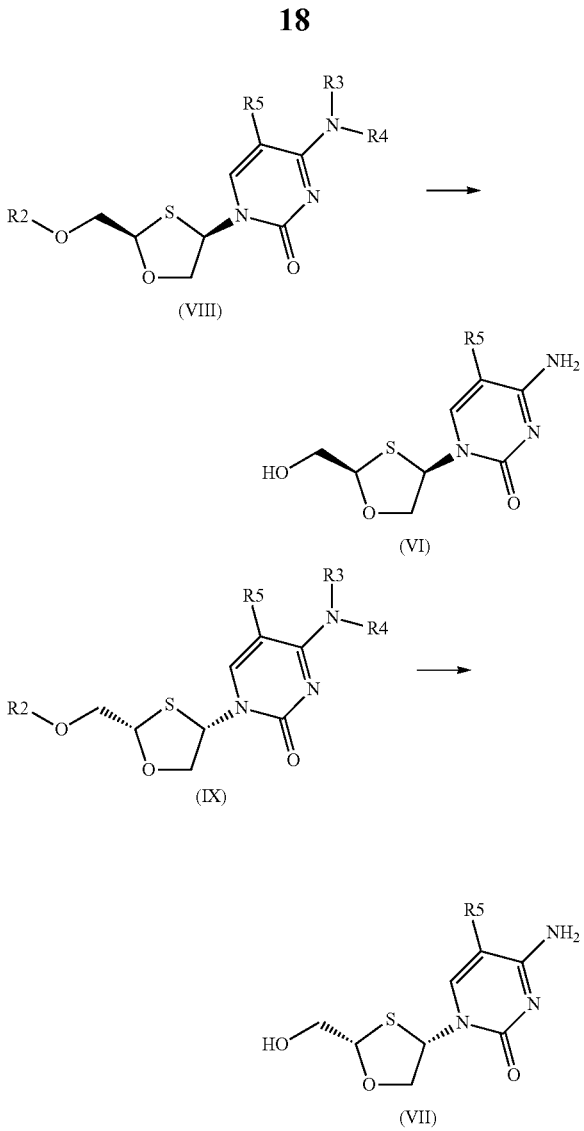

wherein

R2 is H, $C(O)C_{1-6}$alkyl, $C(O)OC_{1-6}$alkyl, $C(O)C_{6-12}$aryl, $C(O)OC_{6-12}$aryl, $C(O)C_{6-12}$arylalkyl, $C(O)OC_{6-12}$arylalkyl, $C(O)C_{1-6}$alkylaryl, $C(O)OC_{1-6}$ alkylaryl, or a silyl protecting group of general formula SiR7R8R9 wherein R7, R8 and R9 are each independently selected from $C_{1-6}$alkyl, aryl or $C_{1-6}$ alkylaryl;

R3 and R4 are each individually selected from H or benzoyl, provided that when R3 is H, R4 is not H and when R4 is H, R3 is not H; and R5 is H, Br, Cl, F, I or $CF_3$.

Preferably R2 is an acyl group, more preferably a benzoyl group or an acetyl group.

Preferably R5 is H or F.

In accordance with a seventh aspect, the present invention provides a process for producing a compound of general formula (II) comprising the steps of:

(a) reacting a silylated base of general formula (X) with a 1,3-oxathiolane of general formula (V) to produce a compound of general formula (II) or (III):

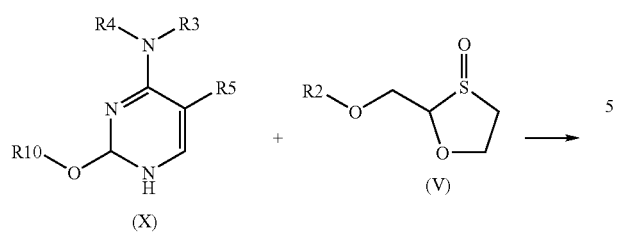

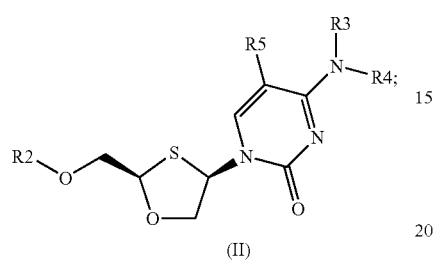

-continued

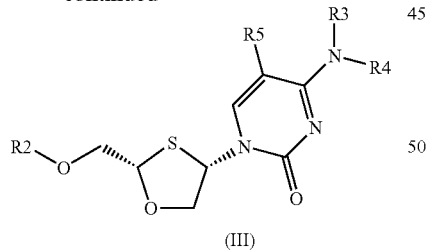

wherein
R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;
R3 and R4 are the same or different and are each individually selected from H or C(O)—R6;
R6 is C$_{6-12}$aryl or C$_{1-6}$alkylaryl in which the C$_{1-6}$alkylaryl is preferably C$_{1-6}$alkylC$_{6-12}$aryl;

R5 is H, Br, Cl, F, I or CF$_3$; and

R10 is a silyl protecting group of general formula SiR7R8R9 as previously defined; and wherein the 1,3-oxathiolane of general formula (V) is the (R)-enantiomer in at least 60% ee; and (b) selective recrystallisation of the compound of general formula (II) from a solvent wherein the solvent is C$_{1-6}$alcohol or mixtures of C$_{1-6}$alcohols.

In a particularly preferred embodiment, R6 is phenyl.

In accordance with an eighth aspect, the present invention provides a process for producing a compound of general formula (VI) comprising the steps of:

(a) reacting a silylated base of general formula (X) with a 1,3-oxathiolane of general formula (V) to produce a compound of general formula (II) or (III):

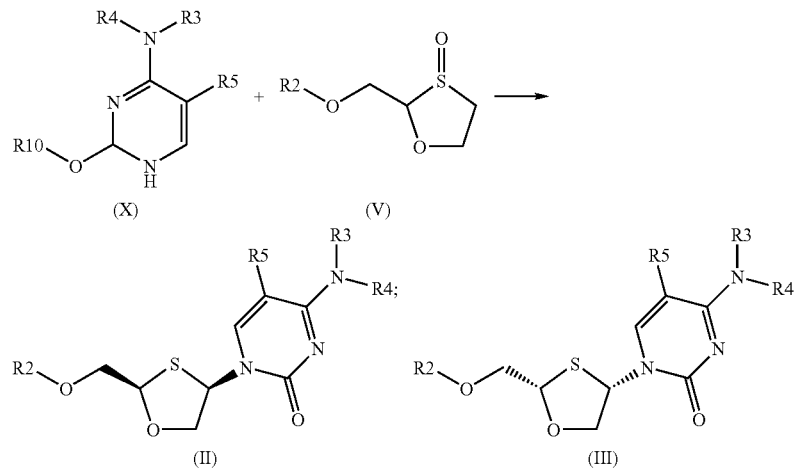

wherein
R2 is H, C(O)C$_{1-6}$alkyl, C(O)OC$_{1-6}$alkyl, C(O)C$_{6-12}$aryl, C(O)OC$_{6-12}$aryl, C(O)C$_{6-12}$arylalkyl, C(O)OC$_{6-12}$ arylalkyl, C(O)C$_{1-6}$alkylaryl, C(O)OC$_{1-6}$alkylaryl, or a silyl protecting group of general formula SiR7R8R9 wherein R7, R8 and R9 are each independently selected from C$_{1-6}$alkyl, aryl or C$_{1-6}$alkylaryl;
R3 and R4 are the same or different and are each individually selected from H or C(O)—R6;
R6 is C$_{6-12}$aryl or C$_{1-6}$alkylaryl in which the C$_{1-6}$alkylaryl is preferably C$_{1-6}$alkylC$_{6-12}$aryl; and
R5 is H, Br, Cl, F, I or CF$_3$; and
R10 is a silyl protecting group of general formula SiR7R8R9 as previously defined; and
wherein the 1,3-oxathiolane of general formula (V) is the (R)-enantiomer in at least 60% ee;
(b) selective recrystallisation of the compound of general formula (II) from a solvent wherein the solvent is C$_{1-6}$alcohol or mixtures of C$_{1-6}$alcohols; and
(c) deprotecting the compound of general formula (II) to produce a compound of general formula (VI):

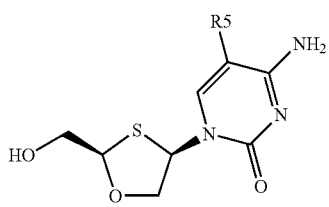

In a particularly preferred embodiment, R6 is phenyl.

In accordance with a ninth aspect the present invention provides a compound of formula (XIII) and diastereomers thereof:

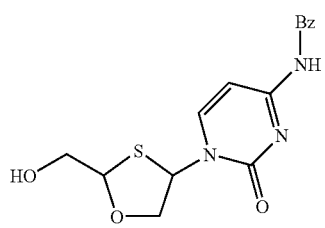

In accordance with a tenth aspect the present invention provides a process for separating a compound of general formula (II) from a compound of general formula (III) comprising the steps of:

(a) providing a mixture of 2-substituted 4-substituted 1,3-oxathiolanes of general formula (II) and (III):

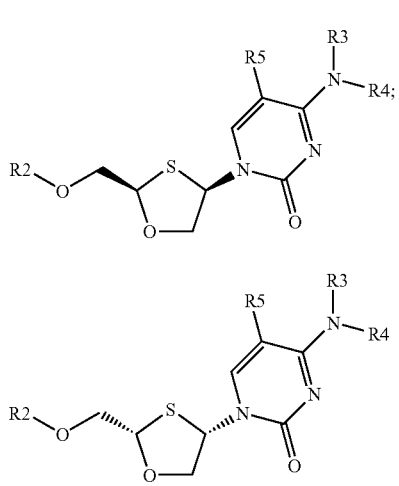

wherein

R2 is H, $C(O)C_{1-6}$alkyl, $C(O)OC_{1-6}$alkyl, $C(O)C_{6-12}$aryl, $C(O)OC_{6-12}$aryl, $C(O)C_{6-12}$arylalkyl, $C(O)OC_{6-12}$ arylalkyl, $C(O)C_{1-6}$alkylaryl, $C(O)OC_{1-6}$alkylaryl, or a silyl protecting group of general formula SiR7R8R9 wherein R7, R8 and R9 are each independently selected from $C_{1-6}$alkyl, aryl or $C_{1-6}$alkylaryl;

R3 and R4 are the same or different and are each individually selected from H or C(O)—R6;

R6 is $C_{6-12}$aryl or $C_{1-6}$alkylaryl in which the $C_{1-6}$alkylaryl is preferably $C_{1-6}$alkyl$C_{6-12}$aryl; and R5 is H, Br, Cl, F, I or $CF_3$; and (b) separating the compound of general formula (II) from the compound of general formula (III) by selective recrystallisation of the compound of general formula (II) from a solvent wherein the solvent is $C_{1-6}$alcohol or mixtures of $C_{1-6}$ alcohols.

In a particularly preferred embodiment, R6 is phenyl.

Definitions

It will be understood by those skilled in the art that the term "alkyl" includes a straight chain or branched alkyl group and may be optionally substituted. Examples of straight chain or branched alkyl groups include but are not limited to methyl, ethyl, propyl, butyl, pentyl, hexyl, iso-propyl, sec-butyl, tert-butyl, di- or tri-alkylated ethyl, propyl, butyl, pentyl or hexyl groups.

"Aryl" includes mono-, bi- or polycyclic ring systems containing an aromatic residue and examples include phenyl, biphenyl and naphthyl. An aryl group may be optionally substituted.

As used herein, the term "alkylaryl" refers to any of mono-, bi- or polycyclic (including conjugated and fused) hydrocarbon ring systems preferably having 6 to 10 carbon atoms and containing an aromatic residue together with an alkyl linkage. Suitable alkylaryl groups include, but are not limited to, benzyl (i.e. —$CH_2$phenyl).

"Acyl" will be understood to mean a group containing the carboxyl C=O moiety though not being a carboxylic acid, ester or amide. Acyl groups include, but are not limited to, the acetyl group and benzoyl group.

"Silyl protecting groups" will be familiar to the skilled addressee as provided for example in Greene, T. W. and Wuts, P. G. M "Protective groups in organic synthesis" ($3^{rd}$ Edition) 1999 John Wiley & Sons Inc.

General synthesis of 2-substituted 4-substituted 1,3-oxathiolanes

The synthesis of a 2-substituted 4-substituted 1,3-oxathiolane may be carried out by a number of methods to provide a mixture of the four stereoisomers, these being the two cis isomers and the two trans isomers, in proportions as shown in Table 1.

TABLE 1

| Experiment | Scale | Mass recovery | Purity (NMR) | cis:trans ratio | cis yield |
|---|---|---|---|---|---|
| 1 | 5 g | 89% | 69% | 2.8:1 | 45% |
| 2 | 5 g | 89% | 70% | 2.5:1 | 45% |
| 3 | 10 g | 86% | 62% | 2.9:1 | 40% |
| 4 | 10 g | 84% | 67% | 2.6:1 | 41% |

In accordance with the present invention, a compound of general formula (II) or (III) is produced by reacting a base of general formula (IV) with a 1,3-oxathiolane of general formula (V) to produce a compound of general formula (II) or (III) as shown in Scheme 1:

Scheme 1: Synthesis of optically active compounds (II) and (III) by reaction of a base (IV) with a 1,3-oxathiolane (V)

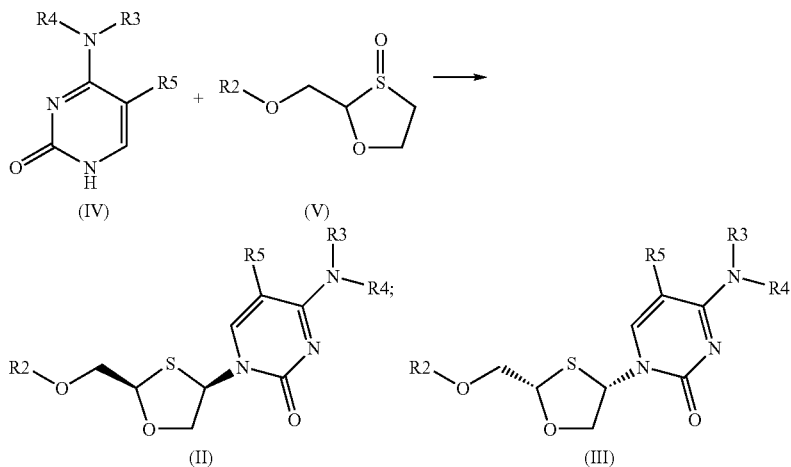

A compound of general formula (II) or (III) may also be produced by reacting a silylated base of general formula (X) with a 1,3-oxathiolane of general formula (V) as shown in Scheme 2 where R10 is a silyl protecting group.

Scheme 2: Synthesis of optically active compounds (II) and (III) by reaction of silyated base (X) with a 1,3-oxathiolane (V)

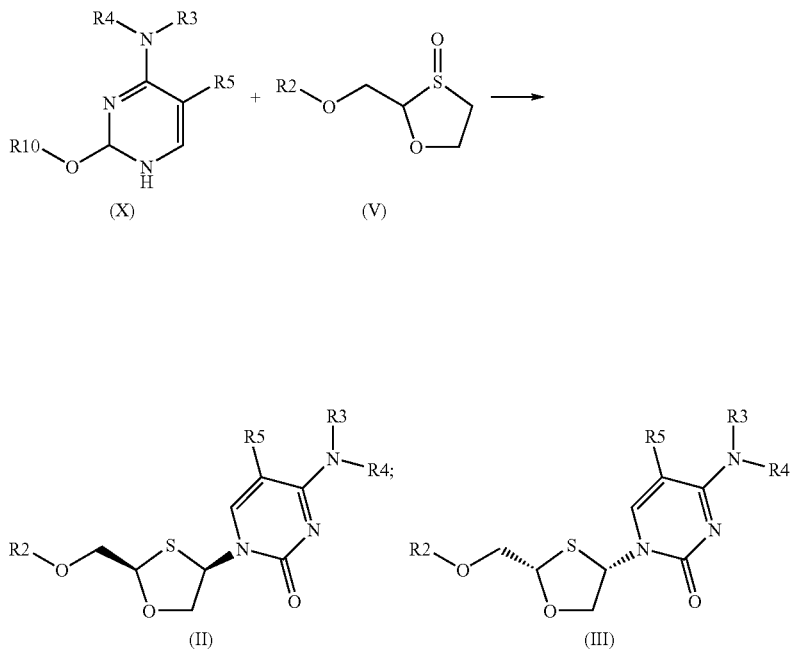

The 1,3-oxathiolane of general formula (V) is at least 60% ee of the (R) enantiomer, preferably at least 70%, more preferably greater than 85% ee, even more preferably greater than 95% ee and still more preferably greater than 99% ee. The skilled addressee will appreciate that the amount of compound (II) and compound (III) obtained from the reactions illustrated in Schemes 1 and 2 will depend on the %ee of the (R) enantiomer compound (V). When the %ee of the (R) enantiomer of compound (V) is, for example, greater than 95%, then the (R,R) cis isomer of general formula (II) will be the major isomer formed. As the %ee of the (R) enantiomer of compound (V) decreases the amount of compound (II) formed decreases and the amount of compound (III) increases accordingly. The trans isomers are also formed in the process.

Particularly preferred general reaction conditions according to an embodiment of the invention involves the coupling of N-benzoylcytosine (2) with 2-benzoyloxymethyl-1,3-oxathiolane-S-oxide (1) in the presence of trimethylsilyliodide (TMSI), triethylamine and catalytic amounts of copper(II) chloride in dichloromethane (Scheme 3).

Scheme 3: Reaction of N-benzylcytosine with 2-benzoyloxymethyl-1,3-oxathiolane-S-oxide

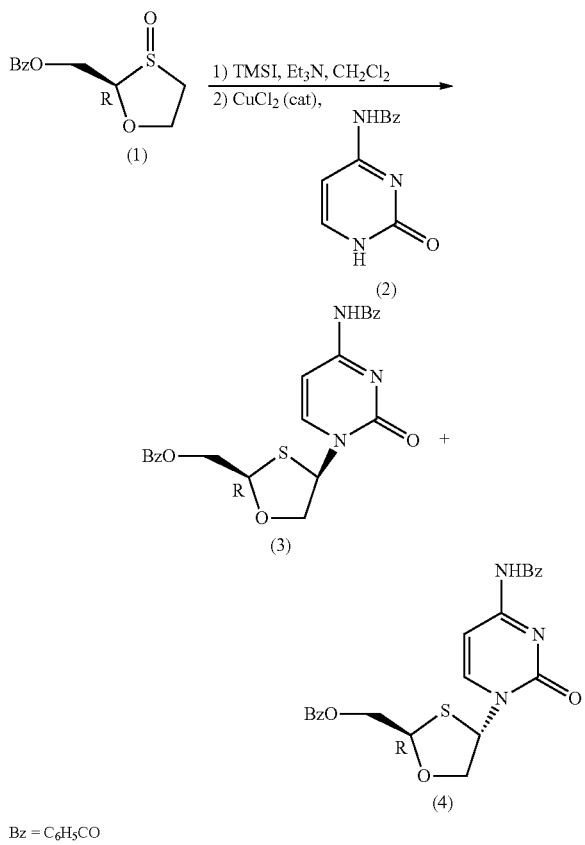

Bz = C₆H₅CO

The reaction proceeds through initial activation of (1) undergoing a Sila-Pumerrer rearrangement. Copper(II)chloride is believed to play a role on inducing a β attack of silylated benzoyl cytosine, resulting in an increase in cis selectivity during the coupling. However this increase in cis selectivity is modest and the amount of CuCl₂ can be reduced without a significant effect on the reaction. The Sila-Pummerrer rearrangement of (1) is conducted at −50° C. and the coupling with the base to proceed at 0° C. overnight, before warming to room temperature and quenching.

The quenched crude reaction mixture was filtered through celite which reduced the problem of solid formation which can complicate the workup process. The filtered reaction mixture was washed with dilute aqueous ammonia and dilute phosphoric acid. The resulting crude reaction mixture was purified by recrystallizing in methanol. Recrystallization in methanol gives the desired cis isomer almost exclusively. Recrystallization in methanol also enhances the optical purity and by using the technique of entrainment, optical purity can be improved further. This finding is particularly useful when starting with less optically pure starting material and is a particularly important finding of the present invention.

Selective Recrystallisation

The inventors have found that a correct choice of the groups R2, R3 and R4 is required for selective recrystallisation of an optically active compound of general formula (II) or (III) from the mixture. The choice of recrystallisation solvent is also dependent on the nature of the groups R2, R3 and R4.

Cytosine protected with acetyl, isobutyrylcarbonyl, pivalylcarbonyl, cyclohexylcarbonyl, p-toluoyl and benzoyl groups was coupled with BOMO-sulfoxide as shown in Scheme 4.

Scheme 4: Coupling of protected cytosine with BOMO-sulfoxide

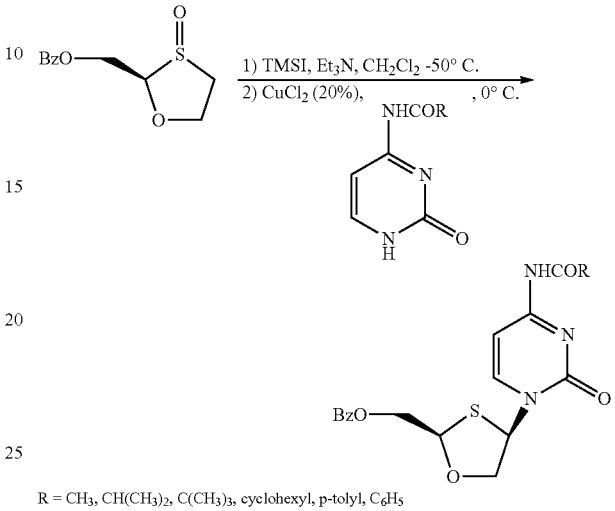

R = CH₃, CH(CH₃)₂, C(CH₃)₃, cyclohexyl, p-tolyl, C₆H₅

For example, when R2 is benzoyl, R5=H, R3=H and R4=Acetyl, recrystallisation from a mixture of cis isomers (R,R and S,S) (compounds II and III) and trans isomers (R,S and S,R) (compounds XI and XII) does not give any separation as shown in Table 2. It was found that the benzoyl protected cytosine coupled product crystallizes efficiently with high cis selectivity.

TABLE 2

| Experiment | R4 | NMR purity | cis:trans ratio | cis yield | Recrystallisation |
|---|---|---|---|---|---|
| Summary expt1-4 | benzoyl | 62-70% | 2.5-2.8:1 | 40-45% | Recrystallisation gave II in >99:1 ratio |
| 5 | acetyl | 66% | 2.26:1 | 46% | Recrystallisation did not give II |
| 6 | isobutyryl | 64% | 2.74:1 | 47% | No recrystallisation from MeOH |
| 7 | pivalyl | 64% | 2.79:1 | 47% | No recrystallisation from MeOH |

By correct choice of the groups R2, R3 and R4 conditions can be selected that lead to the selective resolution of a compound of, for example, formula (II) by recrystallisation from a mixture of all four stereoisomers. As shown in Table 2, where R2=benzoyl and R3=H, and if R4 is varied as follows then R4=benzoyl was found to give the recrystallisation to chirally pure compound, while R4=acetyl or pivalyl or isobutyryl failed to selectively recrystallise the desired chirally pure compound.

Accordingly, in a preferred embodiment of the process according to the first, second, third, fourth, sixth, seventh, eighth and tenth aspects of the present invention, R3 or R4 of the compound of general formula II or III is benzoyl. In a preferred embodiment, R2 of the compound of general formula II or III is also benzoyl.

Cis Selective Recrystallisation

One of the most attractive advantages of the N-benzoyl route is that the recrystallisations in methanol almost exclusively yield the desired cis(R,R) isomer. Preferred embodiments of the present invention show that at 5 g and 10 g scale reactions when using 0.2 equivalents of $CuCl_2$, the reactions were cis selective with selectivity between 2.86:1 (74%) to 2.5:1 (71%). Recrystallizing in 14-15× volumes of methanol (as compared to the mass of the crude) gave almost exclusively the cis isomer.

Recrystallisation Solvents

The recrystallisation solvent of choice is therefore a $C_{1-6}$ alcohol or mixtures of $C_{1-6}$ alcohols. The $C_{1-6}$ alcohol may be a straight chain or branched chain alcohol. Methanol (MeOH), ethanol (EtOH), propanol and butanol are preferred and of these, methanol is particularly preferred. As shown in Tables 3 and 4, MeOH is particularly preferred to give the compound (II) in ee of greater than 99%.

TABLE 3

| Experiment | Recrystallisation method | cis:trans ratio | cis yield | cis recovery, |
|---|---|---|---|---|
| 1 | x15 volumes MeOH | >99:1 | 4.1 g | 87% |
| 2 | x15 volumes MeOH | >99:1 | 4.0 g | 85% |
| 3 | x14.5 volumes MeOH | >99:1 | 7.2 g | 88% |
| 4 | x11 volumes MeOH | >98:2 | 4.6 g | 93% |

TABLE 4

| Mass Recovery | NMR Purity | C/T Ratio | Recrystallization Method | C/T Ratio (After Recrystallization) | cis Yield |
|---|---|---|---|---|---|
| 84-89% | 62-70% | 2.5-2.9:1 | Refluxing Methanol (×10-15 vol) | >98-99:1 | 35-39% |

Mixed Solvent Systems

Recrystallizations with entrainment in mixed solvent systems was examined. Mixtures of $C_{1-6}$ alcohols are also preferred recrystallisation solvents including mixtures of MeOH and another $C_{2-6}$ alcohol such as EtOH, propanol, butanol, pentanol and hexanol in a variety of ratios of MeOH:$C_{2-6}$ alcohol from about 2:98 to 98:2, about 5:95 to 95:5, about 10:90 to 90:10, about 20:80 to 80:20 or about 30:70 to 70:30. A preferred ratio of MeOH:$C_{2-6}$ alcohol is 90:10 and particularly preferred is a ratio of MeOH:$C_{2-6}$ alcohol 95:5. It is preferred that the $C_{1-6}$ alcohol or mixtures thereof contains no more than 5% water.

All recrystallizations were seeded at 53° C., 14 mg of seed/g crude, stirred at 1000 rpm, with ×14 volumes of solvent. Recrystallizations were done on a crude mixture coming from a reaction where the starting BOMO R/S ratio was 80/20 (actual R/S ratio: 82:18). The results are shown in Table 5. However, in contrast to the recrystallization results shown in Tables 10 and 11 below, HPLC analysis of crude gave an approximate crude R/S ratio of 86/14. However when R/S ratio decreases, specially below 90:10, there is a propensity for trans isomer to also crystallize (Table 9 below). In this set of experiments, the trans isomer was observed uniformly about 10-12%. Therefore the observed RR/SS ratio was corrected for the presence of RR and SS trans isomers. Regardless, there was a substantial improvement in optical activity. 100% methanol is particularly preferred as shown in Table 5. Mixtures of methanol, for example with 5% 1-propanol or 5% 1-butanol, are also particularly preferred.

TABLE 5

| Expt # | Recrystallization Solvent System | C/T Ratio (NMR) | Observed Purity | | Corrected Optical Purity | |
|---|---|---|---|---|---|---|
| | | | S,S | R,R | SS | RR |
| 1 | Methanol 100% | 88/12 | 2.33 | 97.67 | 2.65 | 97.35 |
| 2 | Methanol 95%, Ethanol 5% | 88/12 | 2.68 | 97.32 | 3.06 | 96.94 |
| 3 | Methanol 95%, 1-Propanol 5% | 89/11 | 2.26 | 97.74 | 2.53 | 97.47 |
| 4 | Methanol 95%, 2-Propanol 5% | 89/11 | 2.97 | 97.03 | 3.33 | 96.67 |
| 5 | Methanol 95%, 1-Butanol 5% | 88/12 | 2.52 | 97.48 | 2.82 | 97.18 |
| 6 | Methanol 95%, 1-Pentanol 5% | 88/12 | 2.95 | 97.05 | 3.36 | 96.64 |
| 7 | Methanol 95%, 1-Hexanol 5% | 88/12 | 2.57 | 97.43 | 3.93 | 96.07 |
| 8 | Methanol 99%, Water 1% | 90/10 | 2.98 | 97.02 | 3.21 | 96.79 |
| 9 | Methanol 95%, Water 5% | 87/13 | 4.6 | 95.4 | 5.24 | 94.76 |

Note:
This set of recrystallizations was done on a crude mixture coming from a reaction where the starting BOMO R/S ratio was 80/20 (actual R/S ratio: 82:18).

Enhancement of Optical Purity

Enhancement of optical purity is a desirable advantage of the present invention making possible the use of a starting material with a lower optical purity to yield a recrystallised product with higher optical purity, leading to a lower production cost.

Repetition of Recrystallisation Step and Entrainment

In a preferred embodiment of the invention, the selective recrystallisation step (b) in accordance with the first, second, third, fourth, seventh, eighth and tenth aspects is repeated at least once. The repetition of the selective recrystallisation step may facilitate an increase in the overall yield of the desired enantiomer as an additional amount of the desired enantiomer may be recovered as a result of the repeated step. It will be understood however that the the recrystallisation step may also be repeated to selectively recrystallise an isomer which was not obtained in the first selective recrystallisation step. Thus, for example, the desired R,R-enantiomer may be selectively recrystallised in the first recrystallisation step and the S,S-enantiomer may be selectively recrystallised in the second recrystallisation step.

In a particularly preferred embodiment, the selective recrystallisation step (b) in accordance with the first, second, third, fourth, seventh, eighth and tenth aspects is an entrainment or a cyclic entrainment process. The inventors have surprisingly found that the yield of a preferred single enantiomer can be increased by entrainment. As demonstrated by the results obtained in Example 3 of the Experimental Section the addition of a small amount of the R,R-enantiomer favours the recrystallisation of the R,R-enantiomer. This seeding or entrainment process therefore advantageously increases the recrystallised yield of the desired enantiomer. The results obtained in Example 3 are shown in Table 6.

TABLE 6

| Expt | Actual Enantiomer Ratio R/S (calculated based on purities of starting BOMOs) | Recrystallization Method | |
|---|---|---|---|
| | | RR/SS ratio without Entrainment | RR/SS ratio with Entrainment |
| 1 | 98.3/1.7 | 99.0-99.4/1.0-0.6 | 99.5-99.8/0.5-0.2 |
| 2 | 94.2/5.8 | 98.14/1.86 | 99.33/0.67 |
| 3 | 90.0/10.0 | 97.67/2.33 | 99.23/0.77 |
| 4 | 81.7/18.3 | 95.1/4.9 | 98.2/1.8 |

In order to examine the optical purity enhancement during the recrystallization, starting 2-benzoyloxymethyl-1,3-oxathiolane-S-oxide (BOMO) (R-BOMO (11) and S-BOMO (18)) samples were analysed by chiral HPLC.

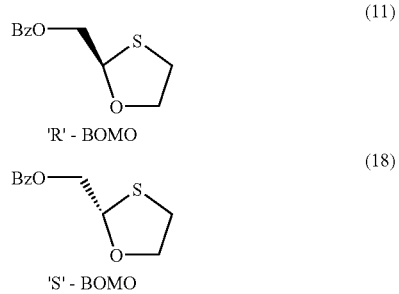

Bz = $C_6H_5CO$

As can be seen from Table 7, supplied BOMOs were of varied purity.

TABLE 7

| BOMO Sample | S % (HPLC) | R % (HPLC) | Actual R/S Ratio |
|---|---|---|---|
| R-1 | 1.72 | 97.60 | 98.3/1.7 |
| S-1 | 84.71 | 11.62 | 12.1/87.9 |
| S-2 | 80.80 | 15.01 | 15.7/84.3 |
| R-3 | 2.51 | 95.33 | 97.4/2.6 |
| R-4 | 2.67 | 96.26 | 97.3/2.7 |

Note that the samples often contained other impurities as well, which is the reason for differing R/S ratios as compared to HPLC analysis.

Optical Purity Enhancement Via Two Recrystallisation

The results from doing two recrystallizations in order to obtain very pure product are shown in Table 8. These recrystallizations were done without entrainment. Interestingly the solubility of the pure product appeared to be lower in methanol as compared to the crude product. This may be because that impurities present could be helping to solubilize the product. For example the crude product could be recrystallized in refluxing (10-15×) methanol readily. However with pure product we found that it was not easy to dissolve product even in ×25 volumes of refluxing methanol, generally we used ×40 volumes of refluxing methanol (in the example below we used ×30 volumes), but still with high recovery.

'Pure' R BOMO (R/S ratio 98.3/1.7) was used in the experiment. The first recrystallization in ×15 volumes of methanol yielded a product with a RR/SS ratio of 99.13/0.87. The $2^{nd}$ recrystallization (in ×30 volumes of methanol) increased the RR/SS ratio to 99.6/0.4 with a recovery of 95%. Because the recovery from the second recrystallization is high a second recrystallization could also be attractive when there is some trans isomer left from the first recrystallization.

TABLE 8

| Starting R/S ratio | $1^{st}$ Recrystallization | | $2^{nd}$ recrystallization | | Recovery in the $2^{nd}$ recrystallization |
|---|---|---|---|---|---|
| | RR isomer | SS isomer | RR isomer | SS isomer | |
| 98.3/1.7 | 99.13 | 0.87 | 99.60 | 0.4 | 95% |

Therefore, the starting BOMO used in the coupling reaction can be of lower purity (i.e. R:S ratio) in view of the ability to increase the RR/SS ratio of the final coupled product using the recrystallisation method of the present invention.

Optical Purity Enhancement Via Entrainment

A racemic mixture of enantiomers can be resolved during the crystallization process. A mixture of enantiomers can crystallize either by the formation of a racemic compound or by the formation of a conglomerate. In a racemic compound, the crystals are in a lattice with a regular arrangement of both enantiomers in equal amounts. However in a conglomerate, molecules of one enantiomer is preferentially attracted to the same enantiomer, thus crystallizes as a physical mixture of crystals belonging to one enantiomer or the other. If the material of interest crystallizes as a conglomerate, then a process known as entrainment (essentially by using the pure crystals as seeds for crystallization of the enantiomer of interest) could be used to preferentially crystallize the desired enantiomer, enhancing the optical purity.

Entrainment could be affected by many variables:
Temperature at which the seeding is conducted: If the temperature is too low, natural crystallization may have started. If the temperature is too high some of the seed crystals added would dissolve;
The amount of seed crystals used;
Purity and the particle size of the seeds;
Rate of stirring during the crystallization;
Time length of stirring;
Volume of the solvent—methanol;
Quality of the crude also could play a role. For example we have found that the pure product is less soluble in methanol than in the presence of impurities.

Optical Purity Enhancement During Recrystallization when the Starting BOMO is an R/S Mixture R/S BOMO mixtures (at different ratios from 100:0 R/S to 50:50) were oxidized to the corresponding S-oxide with $H_2O_2$/HOAc, and then without crystallizing the resulting S-oxide this was coupled with benzoyl cytosine. It was hypothesized that if it was possible for the S-oxide itself to crystallize via conglomerate formation, then, a removed portion from this non-homogeneous mixture may yield a different optical bias than intended. The reaction was worked up the usual way, and the crude was recrystallized with and without entrainment.

First all solvent was removed from the crude material. This was then refluxed in 14 volumes of methanol till all the material was in solution. Next this was allowed to cool with stirring while monitoring the temperature. At the temperature of approximately 55° C., the stirred mixture was seeded with Pure 'R,R' isomer, allowed to come to room temperature and stirred overnight. The crystallized mixture was then filtered, washed with methanol and analyzed via chiral HPLC. As a control an identical sample was refluxed in methanol till all were in solution, and then allowed to cool without any stirring or seeding.

In summary, the results in Table 9 below show that there is a substantial optical purity enhancement during the crystallization, even without entrainment. Even with a starting BOMO R/S ratio of 80/20, the RR/SS ratio, even without entrainment has increased to 95/5. However with entrainment, the enhancement is even higher. Starting BOMO R/S ratio of as low as 90/10 gave a final purity over 99%, while an R/S ratio of 80/20 gave a purity over 98%. This information shows that starting BOMO need not be highly pure to get a high product purity. However it is also interesting to note that as the optical purity of the starting material goes down, the quality of the cis-trans separation also decreases. Generally below R/S ratio of 90/10, trace presence of the trans isomer could be seen (see entries 4 and 5, Table 9). However a second recrystallization should remove this trans isomer as previously discussed.

TABLE 9

| Expt # | Intended BOMO R/S ratio (by manual mixing) | Actual R/S Ratio (calc. based on purities of starting BOMOs) | RR/SS Ratio of the Crude Coupled Product (HPLC analysis) | Presence of Trans after recrystallization (NMR estimation) | Recrystallization Method RR/SS ratio without Entrainment | RR/SS ratio with Entrainment |
|---|---|---|---|---|---|---|
| 1 | 100/0 | 98.3/1.7 | — | No Trans present | 99.0-99.4/ 1.0-0.6 | 99.5-99.8/ 0.5-0.2 |
| 2 | 95/5 | 94.2/5.8 | 96/4 | <1% | 98.14/1.86 | 99.33/0.67 |
| 3 | 90/10 | 90/10 | 94.2/5.8 | <1% | 97.67/2.33 | 99.23/0.77 |
| 4 | 80/20 | 81.7/18.3 | 89.5/10.5 | 2-4% | 95.1/4.9 | 98.2/1.8 |
| 5 | 50/50 | 57/43 | 67/33 | 20% | — | |

NOTE:
When the presence of trans is less than 4-5%, NMR estimation is not accurate due to noise etc., under standard NMR acquisition conditions.

Optical Purity Enhancement During Recrystallization of 'S' BOMO Reactions

With a true conglomerate, entrainment induced optical purity enhancement could occur with either enantiomers. To test this, an analogous reaction with a sulfoxide derived from S enriched BOMO (R/S ratio 12/88) was conducted. The crude reaction mixture derived from the coupling of S-BOMO sulfoxide with benzoyl cytosine was recrystallized with and without entrainment. Indeed the results shown in Table 10 with entrainment were similar to the analogous experiment where R/S ratio was 90/10.

TABLE 10

| Recrystallization Method | Starting Purity (R/S ratio) | % R,R | % S,S |
|---|---|---|---|
| Entrainment | 12.1/87.9 | 1.5 | 98.5 |
| No Entrainment | 12.1/87.9 | 2.2 | 97.8 |

Examination of the Variables Affecting Entrainment Time

Generally a time effect on the optical purity was observed. Standing overnight was found to be optimum and convenient. At 1.5 hours or 3 hours intervals it appeared the crystallization was not complete and thus generally overnight standing was used (Tables 12 and 13). Keeping more than 1 day, while improved the purity, did not improve the purity significantly more.

Table 11 shows the results of a study where crude (Starting R/S ratio: 97/3) was recrystallized with 14 volumes of methanol.

TABLE 11

| | | Optical Purity | |
|---|---|---|---|
| Experiment | Time allowed for crystallization | Recrystallization with seeding (14 mg/g crude) | Recrystallization without seeding or stirring |
| 1 | 1.5 hrs | 99.3/0.7 | 98.4/1.6 |
| 2 | 3 hrs | 98.4/1.6 | 98.4/1.6 |
| 3 | 4 days | 98.6/1.4 | 99.5/0.5 |

Stirring and Seeding

To test the effects of the variables, seeding and stirring, the following experiments were done. Even though the reaction was done using 80:20, R/S mixture of BOMO (actual R/S ratio: 82:18), for these experiments the crude itself was analyzed separately via HPLC.

For these experiments, all solvent is removed from the crude material first. This is then refluxed in 14 volumes of methanol until all material is in solution. Next this is allowed to cool with stirring (at the specified rate) or without stirring, while monitoring the temperature. At the temperature of 55° C., the stirred mixture is seeded with Pure 'R,R' cis isomer or not seeded and stirred overnight while allowing the temperature to come to room temperature. The crystallized mixture is then filtered, washed with methanol and analyzed via HPLC. The results are shown in Table 12. These results show that stirring is always better than no stirring. It may be that stirring could generate seeds and distribute them all over, stirring without adding seeds give higher optical purity products than recrystallizations where seeds had been added, but no stirring is done. Crystallization is essentially complete by 1 day, but purity improves slightly with time (Table 11).

TABLE 12

| | CONDITIONS | | | | | | |
|---|---|---|---|---|---|---|---|
| | | | Seeds | | | RESULTS | |
| Expt # | Standing time (days) | Rate of Stirring (rpm) | Seeded (Yes/No) | Amounts of Seeds (mg of seeds/g crude) | Temperature of seeding ° C. | S,S | R,R |
| 1 | 1 | 1000 | Y | 14 | 55 | 0.83 | 99.17 |
| 2 | 1 | 0 | Y | 14 | 55 | 1.71 | 98.29 |
| 3 | 1 | 1000 | N | — | — | 1.45 | 98.55 |
| 4 | 1 | 0 | N | — | — | 1.81 | 98.19 |
| 5 | 3 | 1000 | Y | 14 | 55 | 0.68 | 99.32 |

Note:
This set of recrystallization was done on a crude mixture coming from a reaction where the starting BOMO R/S ratio was 80/20 (actual R/S ratio: 82:18). However HPLC analysis of crude gave an approximate R/S ratio of 95.3/4.7.

Temperature

The results obtained in Table 13 possibly shows that, at temperatures above 55° C. (or so), seeds partially dissolve. Thus temperatures below 55° C. are better. On the other hand at lower temperatures there is competing natural seeding, especially with high rates of seeding. This also could decrease the effectiveness of entrainment.

TABLE 13

| | CONDITIONS | | | | | | |
|---|---|---|---|---|---|---|---|
| | | | Seeds | | | RESULTS | |
| Expt # | Standing time (days) | Rate of Stirring (rpm) | Seeded (Yes/No) | Amounts of Seeds (mg of seeds/g crude) | Temperature of seeding ° C. | S,S | R,R |
| 1 | 1 | 1000 | Y | 14 | 55 | 0.96 | 99.04 |
| 2 | 1 | 1000 | Y | 14 | 53 | 0.78 | 99.22 |
| 3 | 1 | 1000 | Y | 14 | 50 | 0.96 | 99.04 |
| 4 | 1 | 1000 | Y | 14 | 45 | 0.95 | 99.05 |

Note:
This set of recrystallizations were done on the same crude mixture used for Table 10, coming from a reaction where the starting BOMO R/S ratio was 80/20 (actual R/S ratio: 82:18). However HPLC analysis of crude gave an approximate R/S ratio of 95.3/4.7. No Trans isomer was seen in the recrystallized mixture In yet another preferred embodiment, the 2-substituted 4-substituted 1,3-oxathiolane of general formula (II) or general formula (III) produced or formed in step (a) in accordance with the first, second, third, fourth, seventh, eighth and tenth aspects, is in the form of a conglomerate. The ability of these compounds to form conglomerates is surprising when taking into consideration that only 5% to 10% of racemates belong to the conglomerate forming group (Lorenz, H., et. al., *Journal of the University of Chemical Technology and Metallurgy* (2007) 42(1): 5-16).

Preferably the desired enantiomer which is obtained by any one of the processes according to the first, second, third, fourth, sixth, seventh, eighth and tenth aspects of the invention does not comprise any detectable amount of an undesired isomer.

Deprotection

Having coupled benzoyl cytosine to BOMO, the final step of the synthesis is the removal of the benzoyl protecting groups to obtain the debenzoylated product, for example compound (17) as shown in Scheme 5.

Scheme 5: Debenzoylation reaction

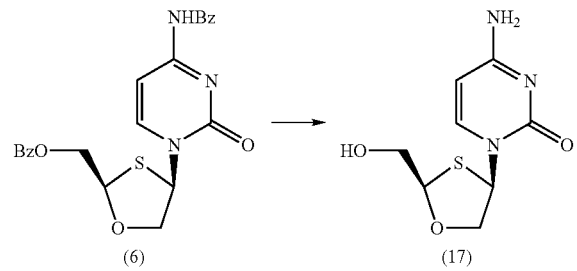

Suitable deprotection methods include: catalytic NaOMe/MeOH, Methanolic Ammonia, and Aqueous Ammonia in Methanol.

The sodium methoxide mediated hydrolysis was investigated first. This method deprotects quantitatively, however requires an aqueous workup to get rid of the salts non-chromatographically. Therefore as the final products, such as compound (17), may possess some water solubility, the workup reduces the yield. The methanolic ammonia method was also investigated. Methanolic ammonia again cleanly deprotected the molecule after overnight stirring, and after removal of the solvent, slurrying in acetone removed the more lipophilic by-products and yielded the product very cleanly. The reaction was equally successful whether the starting material were RR or SS (Table 14, experiments 2, 3, 4). Alternatively, it was found that aqueous ammonia in methanol could also be used. Deprotection using this method is slower but is clean however this involves the removal of water and thus is less convenient in larger scale than methanolic ammonia.

TABLE 14

| Experiment | Method | Product Yield |
|---|---|---|
| 1 | NaOMe (0.1 eq)/MeOH | 61% (8 g scale) (for "RR" cis) |
| 2 | Methanolic Ammonia | 85% (2.2 g scale) (for "RR" cis) |
| 3 | Methanolic Ammonia | 94% (15 g scale) (for "RR" cis) |
| 4 | Methanolic Ammonia | 88% (1 g scale) (for "SS" cis) |
| 5 | Aq Ammonia in Methanol | 86% (3 g scale) (for "RR" cis) |

Compounds

In a preferred embodiment of the fifth aspect of the invention, there is provided novel 2-substituted 4-substituted 1,3-oxathiolane derivatives. The compounds of general formula VIII and IX wherein R2, R3, R4 and R5 are as previously defined:

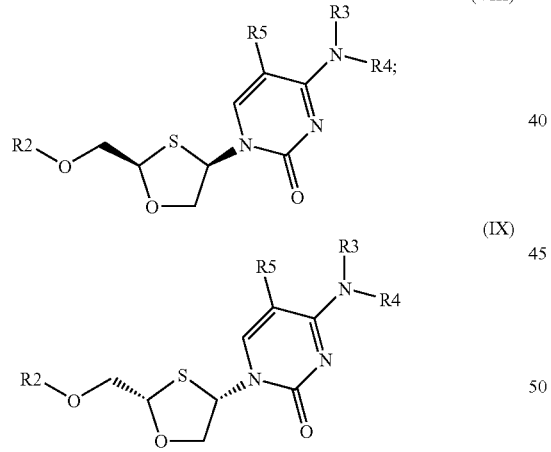

and are preferably selected from the group of compounds consisting of:

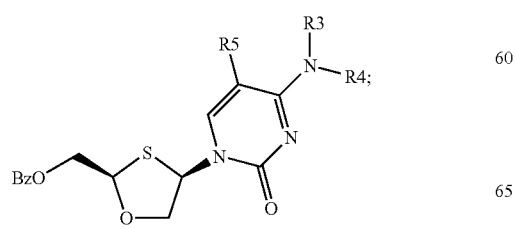

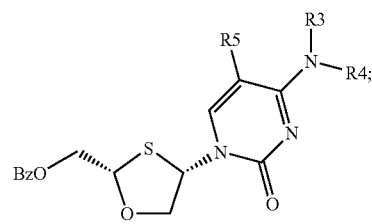

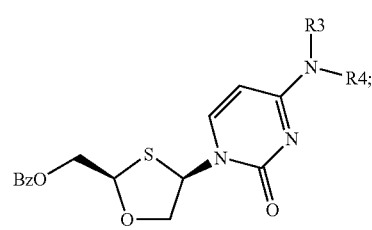

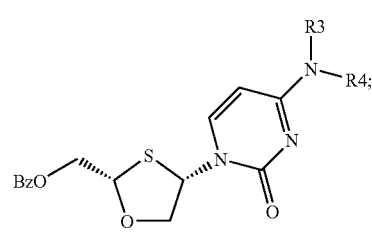

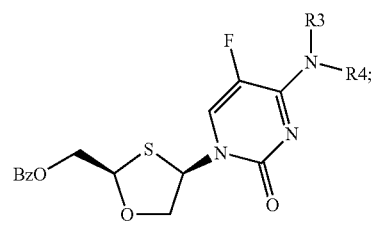

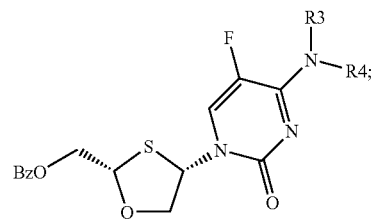

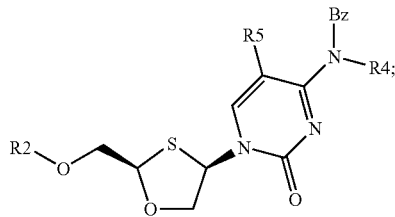

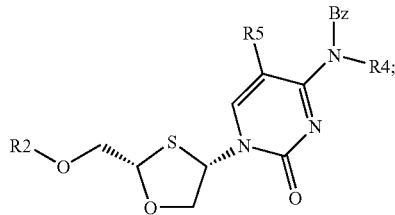

37
-continued
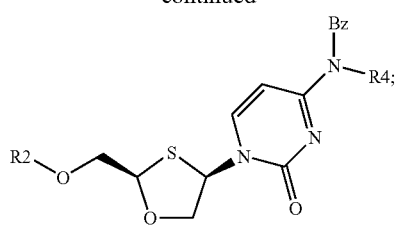
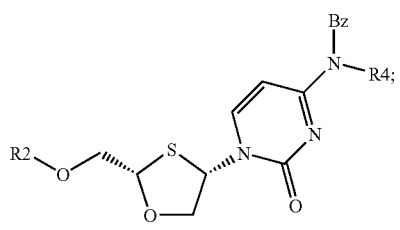
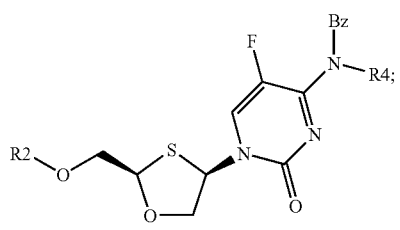
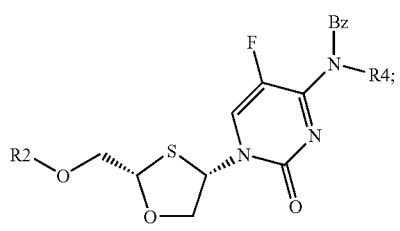
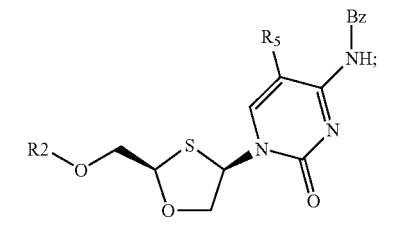
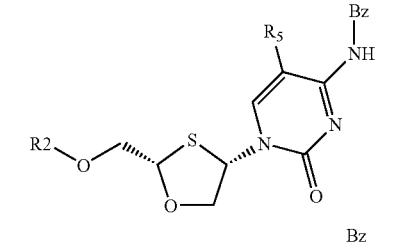
38
-continued
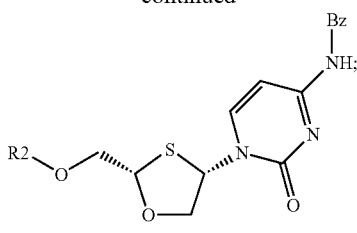
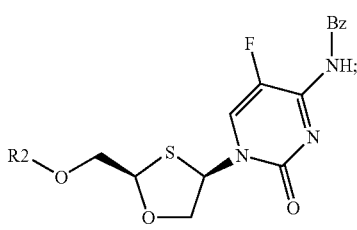
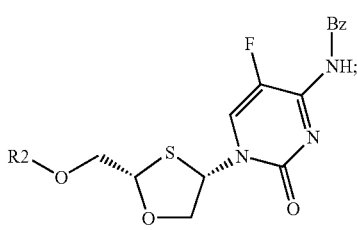
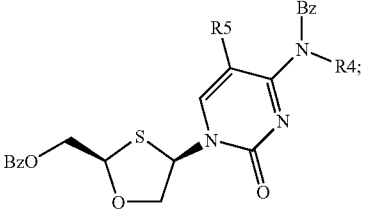
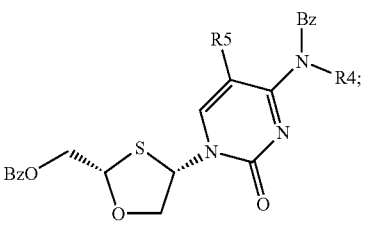
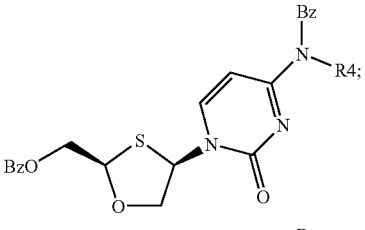
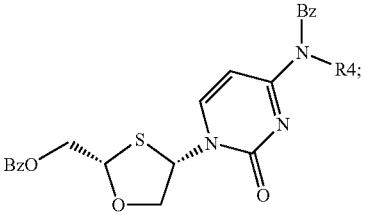

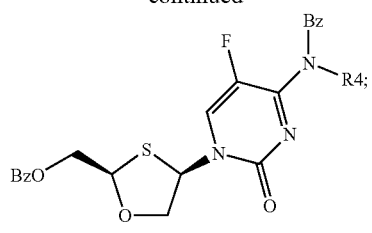
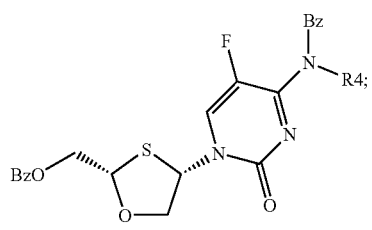
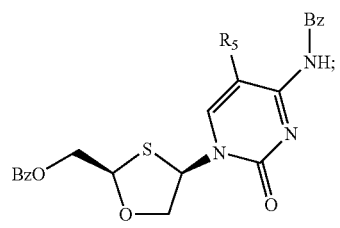
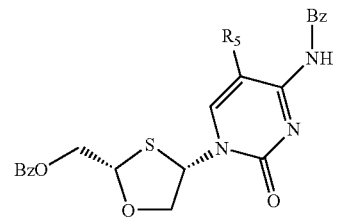
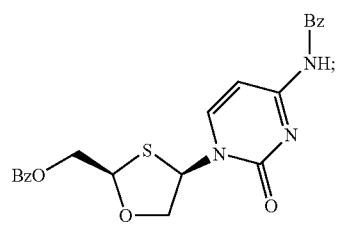
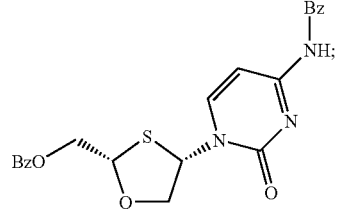
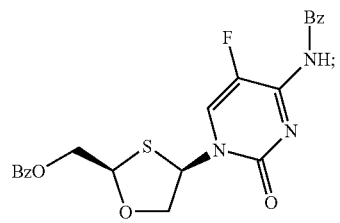
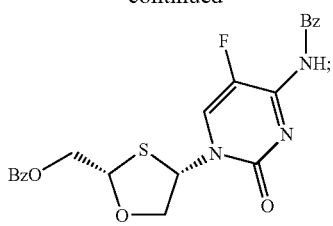
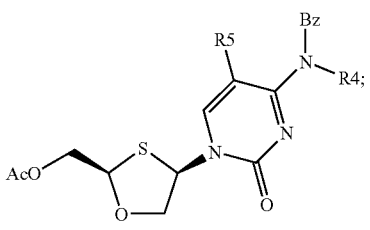
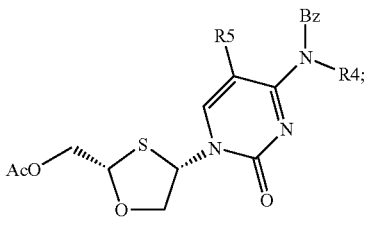
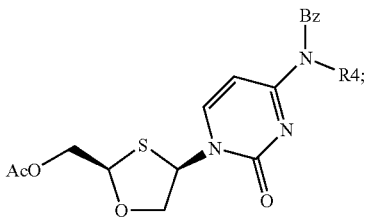
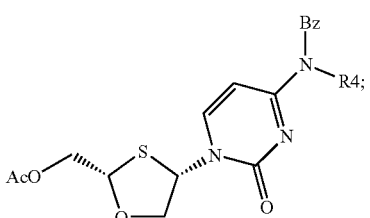
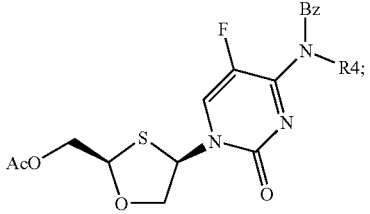
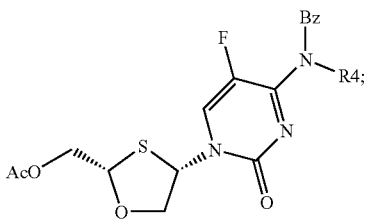

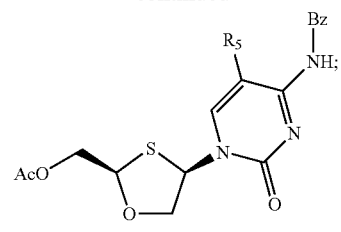
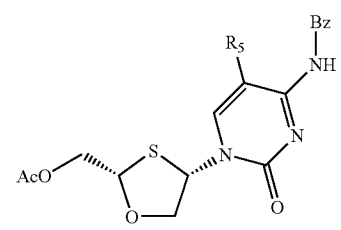
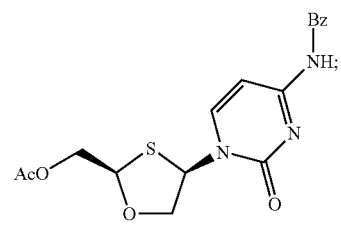
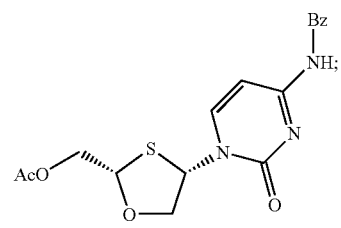
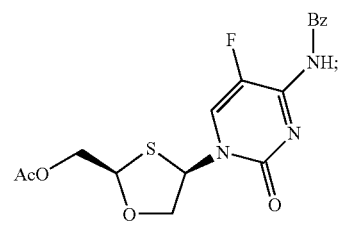
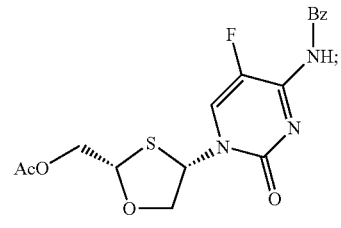
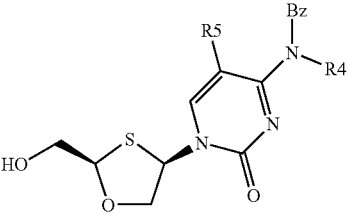
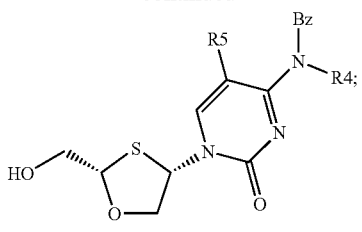
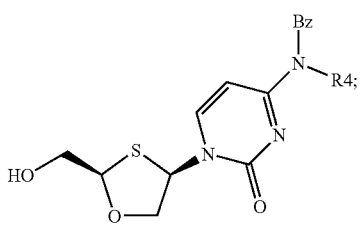
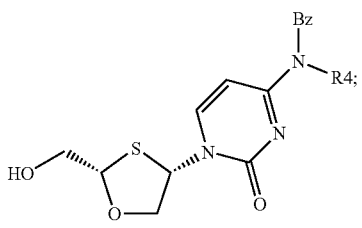
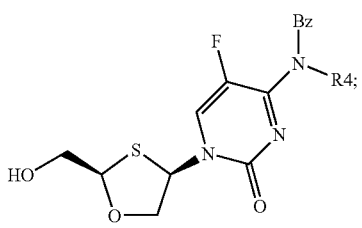
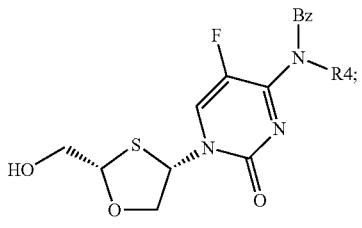
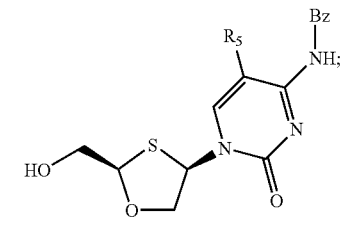
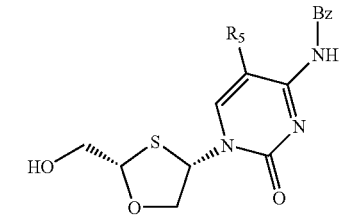

-continued
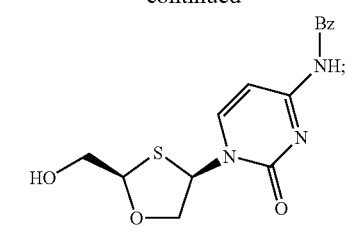
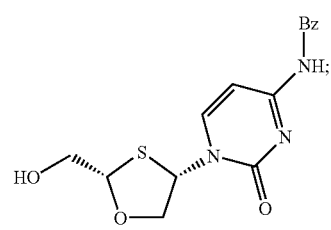
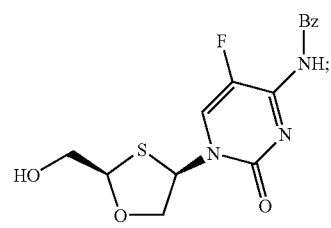
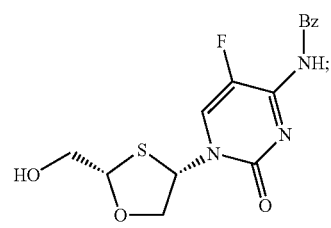
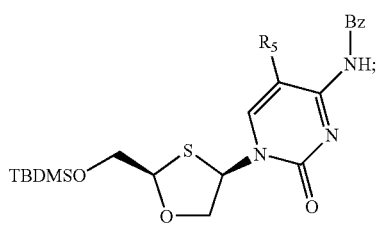
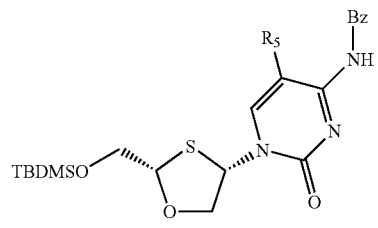
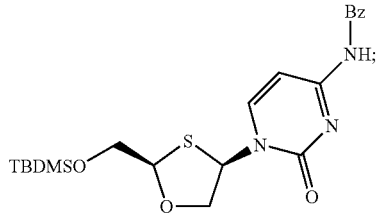
-continued
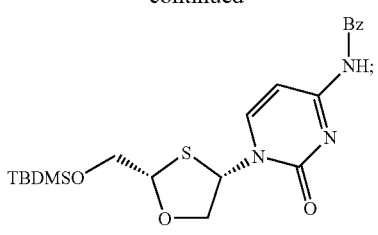
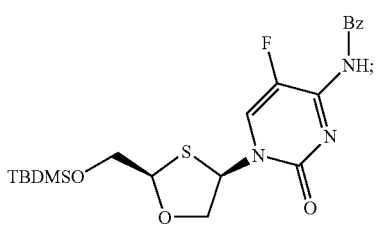
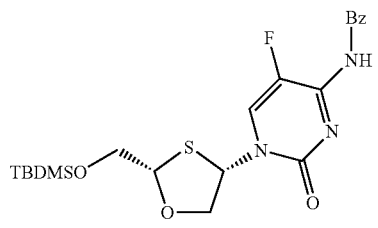
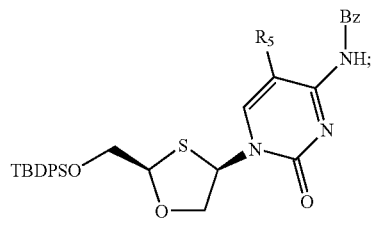
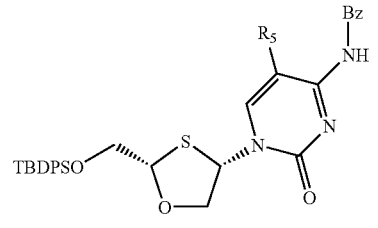
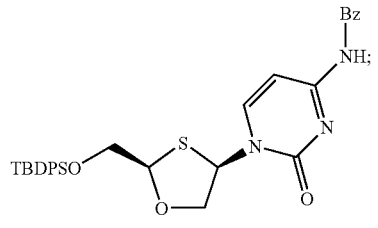
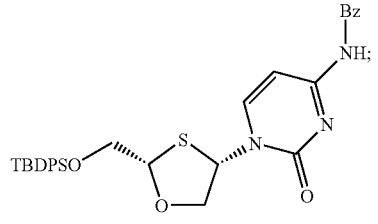

-continued

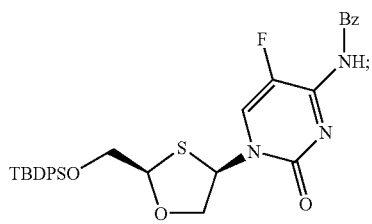

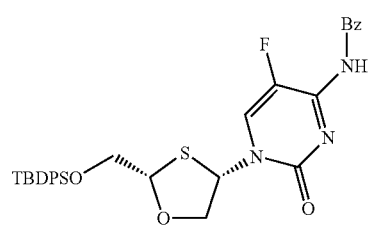

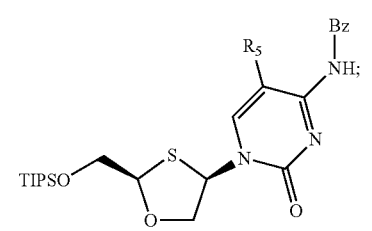

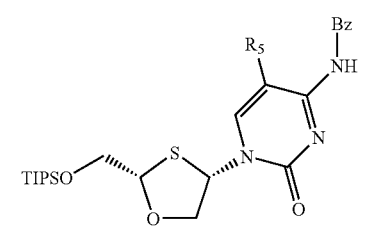

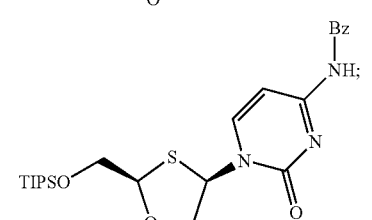

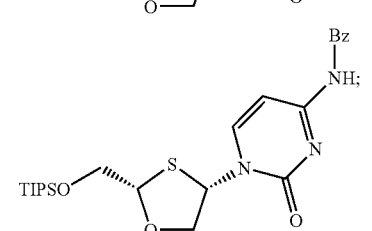

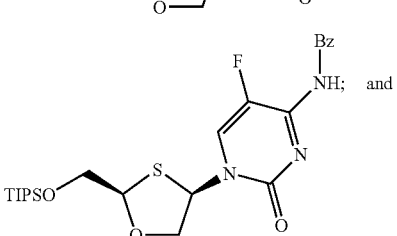

-continued

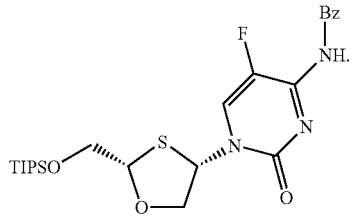

Particularly preferred are N-benzoyl derivatives of compounds of general formula VIII and IX, even more preferred are the N-benzoyl derivatives of formulas:

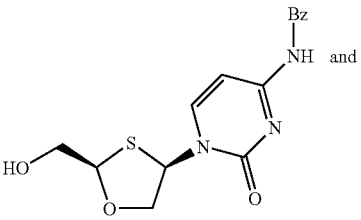

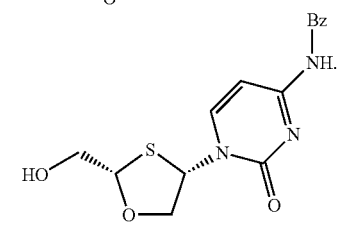

EXAMPLES

The preferred embodiments of the present invention will now be described without limitation by reference to the following Examples.

EXPERIMENTAL

General

All reactions were conducted under a nitrogen atmosphere using oven dried glassware. 2-R and S-Benzoyloxymethyl-1,3-oxathiolane were supplied by Avexa. N-benzoylcytosine was purchased from Shanghai PI Chemicals. TMSI was synthesized in-house and was distilled after the synthesis. Triethylamine was distilled over KOH. The solvents were used without distillation. Low temperatures for reactions were maintained by using a Thermo-Neslab cryostat. The NMR spectra were run on a Varian High Field NMR spectrometer running at 400 MHz. Thin layer chromatography were performed on Machery-Nagel precoated plastic silica gel plates (0.22 mm). HPLC analyses were done on a Waters 510 HPLC system, with a Chiralpak AD, 25 cm×0.46 cm (ID) column, detecting at 254 nm. The solvent system was 20% MeOH in acetonitrile, running isochratically, at a flow rate of 2 mL/min.

Some abbreviations: Eq (equivalents), wrt (with respect to)

Example 1

Synthesis of
2-(R)-Benzoyloxymethyl-1,3-oxathiolane-S-oxide

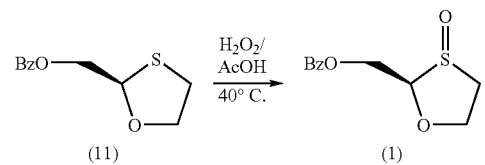

To a stirred mixture of 2-R-Benzoyloxymethyl-1,3-oxathiolane (118 g, 0.526 mol) and glacial acetic acid (47 g, 0.790 mol) in a 500 mL RB flask fitted with an air/water condenser, at 40° C., was added hydrogen peroxide (35% in water) (65 mL, 0.736 mol) in 4 portions at approximately 10 minute intervals. The initial additions are very exothermic. This was stirred at this temperature for 1 hour and at room temperature for 1 hour. The mixture was then transferred to a 1 L beaker and was diluted with dichloromethane (500 mL). While stirring, a solution of 10% sodium sulfite in water (500 mL) was added in small portions (initially vigorous reaction). The organic layer was separated and this was next stirred with an aqueous saturated sodium carbonate solution (500 mL) till there was no bubbling. The organic layer was separated, washed with brine and dried with magnesium sulfate. The resulting hazy colorless solution was filtered through celite to obtain a clear solution. This was evaporated to give the product as colorless viscous oil, which solidified to a white solid. This material was used for the next step in the synthesis without further purification. This material is a mixture of E/Z diastereomers of the ratio 2.4:1 (via NMR). Yield: 114 g (90%)

$^1$H-NMR (CDCl$_3$, 400 MHz): δ=8.05 (d), 7.9 (d), 7.5 (m), 7.4 (m), 4.6-4.8 (m), 4.4 (m), 4.1 (m), 3.2 (m), 3.1 (m), 2.7 (m) ppm. (NMR spectrum is complex due to the presence of E and Z diastereomers)

Example 2

Recrystallization of 2-(R)-Benzoyloxymethyl-1,3-oxathiolane-S-oxide 9.6 g of the E:Z mixture of 2-(R)-Benzoyloxymethyl-1,3-oxathiolane-S-oxide was dissolved in refluxing methanol (12 mL) and was allowed to come to room temperature slowly and allowed to stand overnight. The resulting colorless needle shaped crystals were filtered, washed with ice cold methanol (2 mL), dried. Yield: 3.0 g $^1$H-NMR (CDCl$_3$, 400 MHz): δ=7.9 (d, 2H), 7.6 (m, 1H), 7.4 (m, 2H), 4.6-4.8 (m, 3H), 4.4 (m, 1H), 3.15 (m, 1H), 2.7 (m, 1H) ppm.

Example 3

Synthesis of 2-(R)-benzoyloxymethyl-4-(R)-(N-benzoylcytosin-1-yl)-1,3-oxathiolane (a) Coupling of 2-(R)-benzoyloxymethyl-1,3-oxathiolane-S-oxide with N-benzoyl cytosine

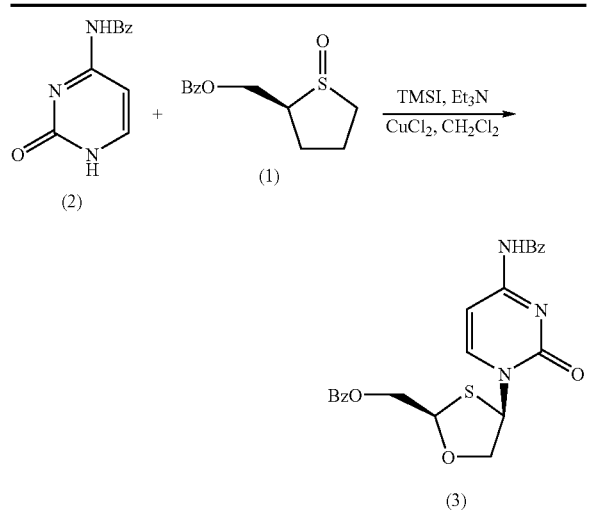

| Reagent | MW | Equivalents | Moles | Amount |
|---|---|---|---|---|
| 2-(R)-benzoyloxymethyl-1,3-oxathiolane-S-oxide | 240.3 | 1.0 | 0.062 | 15.0 g |

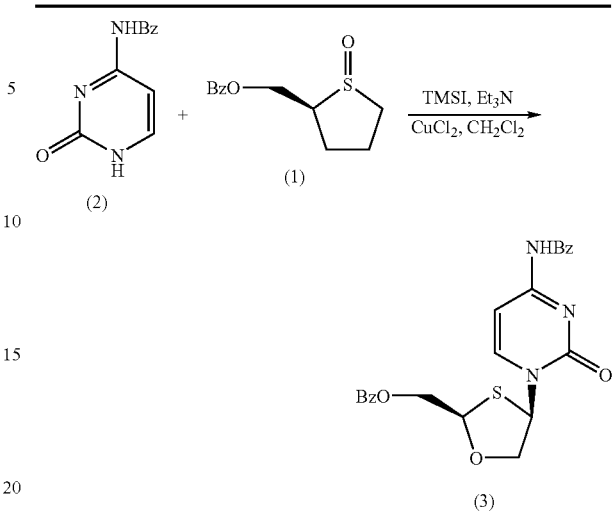

| Reagent | MW | Equivalents | Moles | Amount |
|---|---|---|---|---|
| (2) N-benzoylcytosine(1) | 215.1 | 1.0 | 0.062 | 13.4 g |
| Iodotrimethylsilane | 200.1 d = 1.406 | 3.1 | 0.193 | 38.8 g, 27.6 mL |
| Triethylamine | 101 d = 0.726 | 2.1 | 0.131 | 13.2 g, 18.2 mL |
| Copper(II) chloride(anhydrous) | 134.5 | 0.1 | 0.006 | 0.84 g |
| Dichloromethane | | | | 250 mL |

Rz = C$_6$H$_5$CO 2-(R)-benzoyloxymethyl-1,3-oxathiolane-S-oxide (15.0 g, 0.063 mol) (optical purity of the starting 2-(R)-benzoyloxymethyl-1,3-oxathiolane R/S: 98.3/1.7) was dissolved in dichloromethane (250 mL) in a 500 mL 3-neck flask under nitrogen and this was cooled to −50° C. by means of a cryostat. To this triethylamine (9.6 mL, 0.069 mol, 1.1 equivalent) was added. This was followed by the dropwise addition of iodotrimethylsilane (18.7 mL, 0.131 mol, 2.1 equivalents) via a dropping funnel, at a rate such that the internal temperature remained below −40° C. The resulting light yellow solution was stirred for 30 minutes while maintaining the temperature at −50° C. Next, to the reaction mixture, triethylamine (8.7 mL, 0.062 mol, 1.0 equivalent) was added again followed by the repeat dropwise addition of iodotrimethylsilane (8.9 mL, 0.062 mol, and 1.0 equivalent). Next, oven dried anhydrous copper(II)chloride (0.84 g, 0.0062 mol) was added and after 5 minutes N-benzoylcytosine (13.4 g, 0.062 mol) was added. The resulting mixture was allowed to warm to 0° C. was stirred at this temperature overnight. After overnight stirring, the reaction was allowed to warm to room temperature and stirred at room temperature for 90 minutes. The reaction mixture was quenched with the addition of water (100 mL). This was stirred for 5 minutes, and was filtered through a celite plug. The plug was washed with additional dichloromethane (3×75 mL) and the combined filtrates were poured into a separating funnel. The organic layer was separated, washed sequentially with 5% ammonia in water (2×100 mL), 2% phosphoric acid (2×100 mL) and again with 5% ammonia (100 mL). The combined aqueous layers were re-extracted with dichloromethane (100 mL). The combined organic layers were then washed with 1M sodium thiosulfate (100 mL). The resulting light yellow solution was dried with magnesium sulphate, filtered and evaporated to give a light yellow/brown thick oil 24.3 g (89% recovery). This crude mixture consisted of cis and trans combined coupled product at 75% purity (NMR) and with a cis/trans isomer ratio 2.45:1 (NMR)

(b) Recrystallization of the crude 2-(R)-benzoyloxymethyl-4-(R and S)-(N-benzoylcytosin-1-yl)-1,3-oxathiolane to give pure 2-(R)-benzoyloxymethyl-4-(R)-(N-benzoylcytosin-1-yl)-1,3-oxathiolane Recrystallization with Entrainment To the crude (R)-benzoyloxymethyl-4-(R,S)-(N-benzoylcytosin-1-yl)-1,3-oxathiolane (10.3 g) in a 100 mL round bottom flask, was added 14.0 times (by volume) methanol (144.2 mL) and the mixture was refluxed till a clear solution could be seen. This was then allowed to cool with stirring while monitoring the temperature with a thermometer. When the temperature reached 53° C., the solution was seeded with 144 mg of pure 2-(R)-benzoyloxymethyl-4-(R)-(N-benzoylcytosin-1-yl)-1,3-oxathiolane while vigorously stirring. Following the seeding, the rapidly crystallizing mixture was stirred vigorously overnight. The resulting crystallized product was then filtered, followed by washing with methanol (50 mL). Once all the mother liquor and the subsequent washing had passed through, the resulting crystallized white product was re-washed slowly with methanol (2×100 mL) and dried under vacuum. The resulting white crystalline solid on analyzing with NMR showed that it is >99% the cis isomer. Isolated yield, 4.4 g (44% yield for the recrystallization, based on the crude). Optical purity: RR/SS: 99.3/0.7.

Recrystallization without Entrainment

To the crude (R)-benzoyloxymethyl-4-(R,S)-(N-benzoylcytosin-1-yl)-1,3-oxathiolane (8.0 g) in a 100 mL round bottom flask, was added approximately 14.0 times (by volume) methanol (112 mL) and the mixture was refluxed till a clear solution could be seen. This was then allowed to cool without stirring overnight. The resulting crystallized product was then filtered, followed by washing with methanol (50 mL). Once all the mother liquor and the subsequent washing had passed through, the resulting crystallized white product was re-washed slowly with methanol (2×100 mL) and dried under vacuum. The resulting white crystalline solid on analyzing with NMR showed that it is >99% the cis isomer. Isolated yield, 3.36 g (42% yield for the recrystallization, based on the crude). Optical purity: RR/SS: 98.1/1.9.

Comparison data for recrystallizations with and without entrainment, when the source 2-benzoyloxymethyl-1,3-oxathiolanes (BOMO) used to synthesize the coupling precursor 2-benzoyloxymethyl-1,3-oxathiolane-S-oxides(2) is not enatiomerically pure The comparative data provided in the following table shows that entrainment results in an increased yield of the RR enantiomer.

| Expt | Actual Enantiomer Ratio R/S (calculated based on purities of starting BOMOs) | Recrystallization Method | |
|---|---|---|---|
| | | RR/SS ratio without Entrainment | RR/SS ratio with Entrainment |
| 1 | 98.3/1.7 | 99.0-99.4/1.0-0.6 | 99.5-99.8/0.5-0.2 |
| 2 | 94.2/5.8 | 98.14/1.86 | 99.33/0.67 |
| 3 | 90.0/10.0 | 97.67/2.33 | 99.23/0.77 |
| 4 | 81.7/18.3 | 95.1/4.9 | 98.2/1.8 |

Analytical Data of 2-(R)-benzoyloxymethyl-4-(R)-(N-benzoylcytosin-1-yl)-1,3-oxathiolane $^1$H NMR(CDCl$_3$): δ 8.9 (br s, 1H), 8.25 (d, 1H), 8.0 (d, 2H), 7.8 (d, 2H), 7.6 (m, 2H), 7.45 (m, 4H) 7.3 (poorly resolved d, 1H), 6.6 (d, 1H) 5.5 (t, 1H), 4.8 (m, 2H), 4.5 (d, 1H), 4.05 (dd, 1H)

HPLC Analysis: Column: Chiralpak AD 0.46×25 cm; Solvent System: acetonitrile/methanol 80:20; Flow rate: 2 mL/Min; Wavelength: 254 nm; Retention time for R,R isomer: 11.23 min.

Example 4

Synthesis of 2-(R)-benzoyloxymethyl-4-(R)—(N-benzoylcytosin-1-yl)-1,3-oxathiolane (a) Coupling of 2-(R,S)-benzoyloxymethyl-1,3-oxathiolane with N-benzoyl cytosine

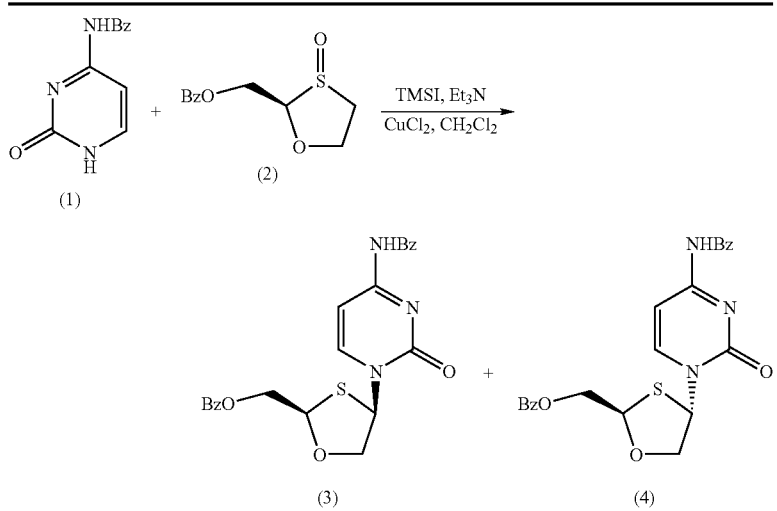

| Reagent | Molecular Weight | Equivalents | Moles | Amount |
|---|---|---|---|---|
| 2-(R)-benzoyloxymethyl-1,3-oxathiolane | 240.3 | 1 | 0.050 | 12.0 g |
| N-benzoylcytosine | 215.1 | 0.95 | 0.047 | 10.1 g |
| Iodotrimethylsilane | 200.1 d = 1.406 | 3 | 0.150 | 30.0 g 21.3 mL |

-continued

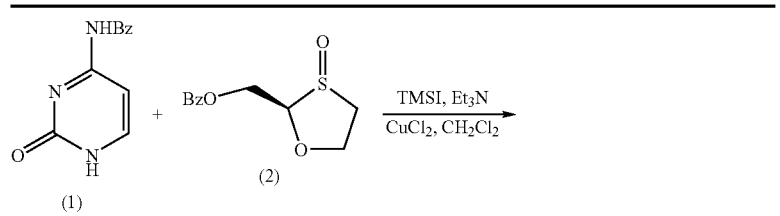

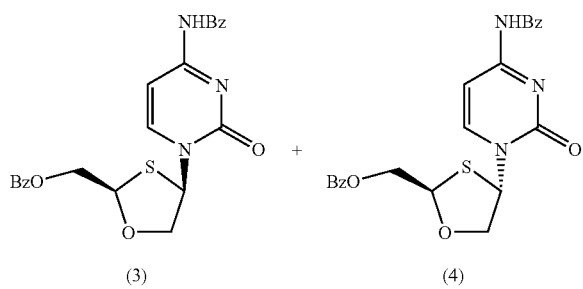

| Reagent | Molecular Weight | Equivalents | Moles | Amount |
| --- | --- | --- | --- | --- |
| Triethylamine | 101 | 2.2 | 0.110 | 11.1 g, |
|  | d = 0.726 |  |  | 15.3 mL |
| Copper(II) chloride | 134.5 | 0.2 | 0.010 | 1.34 g |
| Dichloromethane |  |  |  | 150 mL |

Bz = $C_6H_5O$

Procedure:

To 2-(R,S)-benzoyloxymethyl-1,3-oxathiolane (2) (12.0 g, 0.050 mol) was dissolved in dichloromethane in a 500 mL 3-neck flask and this was cooled to −50° C. To this triethylamine (15.3 mL, 0.110 mol) was added and followed by iodotrimethylsilane (21.4 mL, 0.150 mol) via a dropping funnel, dropwise, at a rate so that the internal temperature was between −30° C. and −50° C. The resulting light yellow solution was stirred for 45 minutes while maintaining the temperature between −40° C. and −50° C. Next, to the reaction mixture, was added copper(II)chloride (1.3 g, 0.010 mol) and after 5 more minutes was added N-benzoylcytosine (1) (10.1 g, 0.047 mol). The resulting mixture was stirred at −50° C. for 15 minutes and then was allowed to warm to 0° C. over 1 hour. The reaction mixture was stirred at this temperature overnight. After overnight stirring, the reaction was stirred at room temperature for 1 hour, cooled again in ice, quenched with the addition of water (100 mL) followed by 5% ammonia (100 mL). This was stirred for 5 minutes, diluted with dichloromethane (50 mL) and filtered through a celite plug. The plug was washed with additional dichloromethane (2×50 mL) and the combined filtrates were poured into a separating funnel. The organic layer was separated, washed with 2% phosphoric acid (2×60 mL) and again with 2.5% ammonia (2×100 mL). The combined aqueous layers were re-extracted with dichloromethane (100 mL). The combined organic layers were dried with magnesium sulphate, filtered and evaporated to give a light yellow/brown thick oil 17.8 g (86% recovery). This crude mixture consisted of cis (3) and trans (4) combined coupled product at 62% purity (NMR) and with a cis/trans isomer ratio 2.86:1 (NMR)

(b) Recrystallization of the crude 2-(R,S)-benzoyloxymethyl-4-(R,S)-(N-benzoylcytosin-1-yl)-1,3-oxathiolane to give pure 2-(R)-benzoyloxymethyl-4-(R)-(N-benzoylcytosin-1-yl)-1,3-oxathiolane

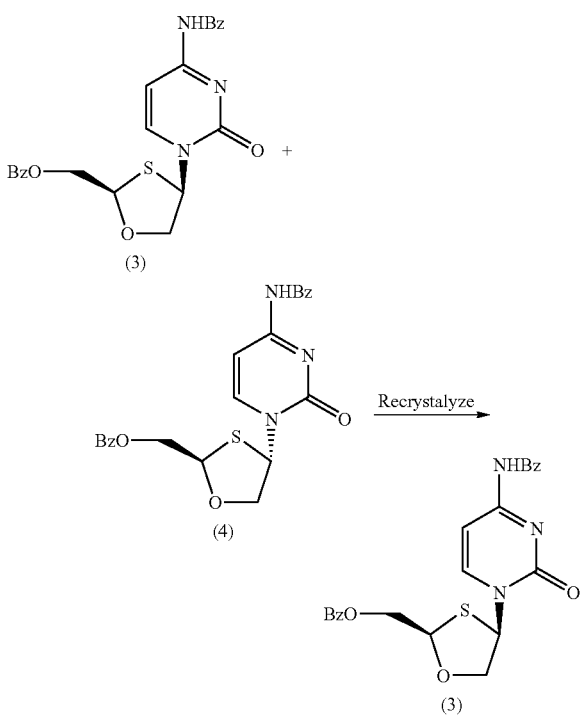

To the crude (R,S)-benzoyloxymethyl-4-(R,S)-(N-benzoylcytosin-1-yl)-1,3-oxathiolane (17.8 g) in a 500 mL round bottom flask, was added 14.5 times (by volume) methanol (258 mL) and the mixture was refluxed till a clear solution could be seen. This was then allowed to cool to room temperature gradually and was left standing overnight. The resulting crystallized product was filtered, followed by washing with methanol (2×100 mL) and drying under vacuum. The resulting slightly coloured feathery crystalline solid on analysing with NMR showed that it is >99% the cis isomer (3). Isolated yield, 7.2 g (35% yield for the cis isomer).

$^1$NMR(CDCl$_3$): δ 8.5 (br s, 1H), 8.25 (d, 1H), 8.0 (d, 2H), 7.8 (d, 2H), 7.6 (m, 2H), 7.45 (m, 4H) 7.3 (poorly resolved d, 1H), 6.6 (d, 1H) 5.5 (t, 1H), 4.8 (m, 2H), 4.5 (d, 1H), 4.05 (dd, 1H)

HPLC Analysis: Column: Chiralpak AD, 25 cm×0.46 cm (ID); Solvent: 20% MeOH in acetonitrile; Flow rate: 1 ml/min; Wavelength: 254 nm; Enatiomeric Purity: >100:1

Example 5

Synthesis of 2-(S)-benzoyloxymethyl-4-(S)—(N-benzoylcytosin-1-yl)-1,3-oxathiolane (a) Coupling of 2-(S)-benzoyloxymethyl-1,3-oxathiolane-S-oxide with N-benzoyl cytosine

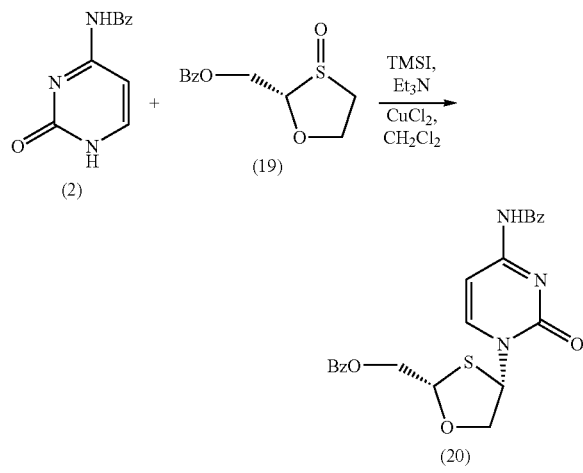

Bz = C$_6$H$_5$CO 2-(R)-benzoyloxymethyl-1,3-oxathiolane-S-oxide (2.0 g, 0.0083 mol) (optical purity of the starting 2-(S)-benzoyloxymethyl-1,3-oxathiolane R/S: 12.1/87.9) was dissolved in dichloromethane (40 mL) in a 100 mL 3-neck flask under nitrogen and this was cooled to −50° C. by means of a cryostat. To this triethylamine (1.27 mL, 0.009 mol, and 1.1 equivalents) was added. This was followed by the dropwise addition of iodotrimethylsilane (2.5 mL, 0.017 mol, 2.1 equivalents) via a dropping funnel, at a rate such that the internal temperature remained below −40° C. The resulting light yellow solution was stirred for 30 minutes while maintaining the temperature at −50° C. Next, to the reaction mixture, triethylamine (1.15 mL, 0.0083 mol, 1.0 equivalent) was added again followed by the repeat dropwise addition of iodotrimethylsilane (1.2 mL, 0.0083 mol, and 1.0 equivalent). Next, oven dried anhydrous copper(II)chloride (0.11 g, 0.0008 mol) was added and after 5 minutes N-benzoylcytosine (1.79 g, 0.0083 mol) was added. The resulting mixture was allowed to warm to 0° C. was stirred at this temperature overnight. After overnight stirring, the reaction was allowed to warm to room temperature and stirred at room temperature for 90 minutes. The reaction mixture was next quenched with the addition of water (25 mL). This was stirred for 5 minutes, and was filtered through a celite plug. The plug was washed with additional dichloromethane (3×25 mL) and the combined filtrates were poured into a separating funnel. The organic layer was separated, washed sequentially with 5% ammonia in water (2×25 mL), 2% phosphoric acid (2×25 mL) and again with 5% ammonia (25 mL). The combined aqueous layers were re-extracted with dichloromethane (25 mL). The combined organic layers were then washed with IM sodium thiosulfate (250 mL). The resulting light yellow solution was dried with magnesium sulphate, filtered and evaporated to give a light yellow/brown thick oil 2.4 g (71% recovery). This crude mixture consisted of cis and trans combined coupled product at 69% purity (NMR) and with a cis/trans isomer ratio 2.4:1 (NMR)

(b) Recrystallization of the crude 2-(S)-benzoyloxymethyl-4-(R and S)—(N-benzoylcytosin-1-yl)-1,3-oxathiolane to give pure 2-(S)-benzoyloxymethyl-4-(S)-(N-benzoylcytosin-1-yl)-1,3-oxathiolane Recrystallization with Entrainment To the crude (S)-benzoyloxymethyl-4-(R,S)—(N-benzoylcytosin-1-yl)-1,3-oxathiolane (2.4 g) in a 100 mL round bottom flask, was added approximately 14.0 times (by volume) methanol (34 mL) and the mixture was refluxed till a clear solution could be seen. This was then allowed to cool with stirring while monitoring the temperature with a thermometer. When the temperature reached 53° C., the solution was seeded with 34 mg of previously recrystallized 2-(S)-benzoyloxymethyl-4-(S)—(N-benzoylcytosin-1-yl)-1,3-oxathiolane while vigorously stirring. Following the seeding, the rapidly crystallizing mixture was stirred vigorously overnight. The resulting crystallized product was then filtered, followed by washing with methanol (10 mL). Once all the mother liquor and the subsequent washing had passed through, the resulting crystallized white product was re-washed slowly with methanol (2×10 mL) and dried under vacuum. The resulting white crystalline solid on analyzing with NMR showed that it is >99% the cis isomer. Isolated yield, 0.96 g (40% yields for the recrystallization, based on the crude). Optical purity: RR/SS: 1.5/98.

Recrystallization without Entrainment

To the crude (S)-benzoyloxymethyl-4-(R,S)—(N-benzoylcytosin-1-yl)-1,3-oxathiolane (13.95 g) in a 250 mL round bottom flask, was added approximately 14.0 times (by volume) methanol (194.6 mL) and the mixture was refluxed till a clear solution could be seen. This was then allowed to cool without stirring overnight. The resulting crystallized product was then filtered, followed by washing with methanol (50 mL). Once all the mother liquor and the subsequent washing had passed through, the resulting crystallized white product was re-washed slowly with methanol (50 mL) and dried under vacuum. The resulting white crystalline solid on analyzing with NMR showed that it is >99% the cis isomer. Isolated yield, 4.8 g (34% yield for the recrystallization, based on the crude). Optical purity: RR/SS: 2.2/97.8.

Example 6

Variables Affecting Entrainment

Experiments were done with crude 2-(R)-benzoyloxymethyl-4-(R)—(N-benzoylcytosin-1-yl)-1,3-oxathiolane.

Effect of Time

Each sample came from a reaction where the starting ratio for the BOMO was 97(R)/3(S) (The R/S ratio of the crude was not done for these samples). The crude was recrystallized by dissolving while refluxing in 14 volumes of methanol. For entrainment 14 mg seeds (pure R,R) per gram of crude were used. Seeding was done at a temperature between 55° C. and 56° C. After the specified time, the crystals were filtered, washed with methanol, dried, and analyzed with HPLC. The results are shown in the following table.

|  |  | Optical Purity | |
| --- | --- | --- | --- |
| Experiment | Time allowed for crystallization | Recrystallization with seeding (14 mg/g crude) | Recrystallization without seeding or stirring |
| 1 | 1.5 hrs | 98.3/0.7 | 98.4/1.6 |
| 2 | 3 hrs | 98.4/1.6 | 99.4/1.6 |
| 3 | 4 days | 98.6/1.4 | 99.5/0.5 |

Effect of Stirring and Seeding

Each sample came from a reaction where the starting ratio for the BOMO was 82 (R)/18 (S). The crude was recrystallized by dissolving while refluxing in 14 volumes of methanol. Next this is allowed to cool with stirring (at the specified rate) or without stirring, while monitoring the temperature. At the temperature of 55° C., the stirred mixture is seeded with Pure 'R,R' isomer or not seeded and stirred overnight while allowing the temperature to come to room temperature. The crystallized mixture is then filtered, washed with methanol and analyzed via HPLC. The results are shown in the following table.

| | CONDITIONS | | | | | | |
| --- | --- | --- | --- | --- | --- | --- | --- |
| | | | Seeds | | | | |
| | Standing time | Rate of Stirring | Seeded | Amounts of Seeds (mg of seeds/g | Temperature of seeding | RESULTS | |
| Expt # | (days) | (rpm) | (Yes/No) | crude) | ° C. | S,S | R,R |
| 1 | 1 | 1000 | Y | 14 | 55 | 0.83 | 99.17 |
| 2 | 1 | 0 | Y | 14 | 55 | 1.71 | 98.29 |
| 3 | 1 | 1000 | N | — | — | 1.45 | 98.55 |
| 4 | 1 | 0 | N | — | — | 1.81 | 98.19 |
| 5 | 3 | 1000 | Y | 14 | 55 | 0.68 | 99.32 |

Note:
This set of recrystallizations were done on a crude mixture coming from a reaction where the starting BOMO R/S ratio R/S ratio: 82:18. However HPLC analysis of crude gave an approximat R/S ratio of 95.3/4.7. No Trans isomer was seen in the recrystallized mixture Effect of Temperature Each sample came from a reaction where the starting ratio for the BOMO was 82 (R)/18 (S). The crude was recrystallized by dissolving while refluxing in 14 volumes of methanol. Next this is allowed to cool with stirring (at 1000 rpm) or without stirring, while monitoring the temperature. At the specified temperature of 55° C., the stirred mixture was seeded with Pure 'R,R' isomer stirred overnight while allowing the temperature to come to room temperature. The crystallized mixture is then filtered, washed with methanol and analyzed via HPLC. The results are shown in the following table.

| | CONDITIONS | | | | | | |
| --- | --- | --- | --- | --- | --- | --- | --- |
| | | | Seeds | | | | |
| | Standing time | Rate of Stirring | Seeded | Amounts of Seeds (mg of seeds/g | Temperature of seeding | RESULTS | |
| Expt | (days) | (rpm) | (Yes/No) | crude) | ° C. | S,S | R,R |
| 1 | 1 | 1000 | Y | 14 | 55 | 0.96 | 99.04 |
| 2 | 1 | 1000 | Y | 14 | 53 | 0.78 | 99.22 |

-continued

| | | | CONDITIONS | | | | |
|---|---|---|---|---|---|---|---|
| | | | | Seeds | | | |
| | Standing time | Rate of Stirring | Seeded | Amounts of Seeds (mg of seeds/g | Temperature of seeding | RESULTS | |
| Expt | (days) | (rpm) | (Yes/No) | crude) | °C. | S,S | R,R |
| 3 | 1 | 1000 | Y | 14 | 50 | 0.96 | 99.04 |
| 4 | 1 | 1000 | Y | 14 | 45 | 0.95 | 99.05 |

Note:
This set of recrystallizations were done on the same crude mixture used for Table 16, coming from a reaction where the starting BOMO R/S ratio was 80/20 (actual R/S ratio: 82:18). However HPLC analysis of crude gave an approximate R/S ratio of 95.3/4.7. No Trans isomer was seen in the recrystallized mixture

Example 7

Recrystallization in Mixed Solvent Systems

All recrystallizations were seeded at 53° C., 14 mg of seed/g crude, stirred at 1000 rpm, with ×14 volumes of solvent. Recrystallizations were done on a crude mixture coming from a reaction where the starting BOMO R/S ratio was 82:18. HPLC analysis of crude gave an approximate crude R/S ratio of 86/14. As previously discussed, when R/S ratio decreases, specially below 90:10, there is a propensity for trans isomer to also crystallize (Table 11). Thus In this set of experiments, we did see the trans isomer uniformly about 10-12%. Therefore the observed RR/SS ratio was corrected for the presence of RR and SS trans isomers. The results are shown in the following table.

| Expt # | Recrystallization Solvent System | C/T Ratio (NMR) | Observed Purity S,S | Observed Purity R,R | Corrected Optical Purity SS | Corrected Optical Purity RR |
|---|---|---|---|---|---|---|
| 1 | Methanol 100% | 88/12 | 2.33 | 97.67 | 2.65 | 97.35 |
| 2 | Methanol 95%, Ethanol 5% | 88/12 | 2.68 | 97.32 | 3.06 | 96.94 |
| 3 | Methanol 95%, 1-Propanol 5% | 89/11 | 2.26 | 97.74 | 2.53 | 97.47 |
| 4 | Methanol 95%, 2-Propanol 5% | 89/11 | 2.97 | 97.03 | 3.33 | 96.67 |
| 5 | Methanol 95%, 1-Butanol 5% | 88/12 | 2.52 | 97.48 | 2.82 | 97.18 |
| 6 | Methanol 95%, 1-Pentanol 5% | 88/12 | 2.95 | 97.05 | 3.36 | 96.64 |
| 7 | Methanol 95%, 1-Hexanol 5% | 88/12 | 2.57 | 97.43 | 3.93 | 96.07 |
| 8 | Methanol 99%, Water 1% | 90/10 | 2.98 | 97.02 | 3.21 | 96.79 |
| 9 | Methanol 95%, Water 5% | 87/13 | 4.6 | 95.4 | 5.24 | 94.76 |

Note:
This set of recrystallization were done on a crude mixture coming from a reaction where the starting BOMO R/S ratio was 80/20 (actual R/S ratio: 82:18). HPLC analysis of crude gave an approximate crude R/S ratio of 86/14).

Example 8

Synthesis of 2-(R)-hydroxymethyl-4-(R)-(cytosin-1-yl)-1,3-oxathiolane

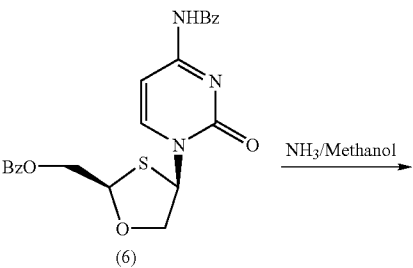

(6)

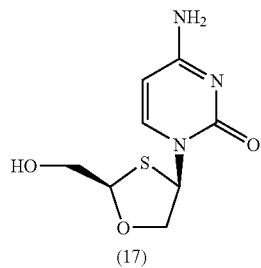

(17)

2-(R)-benzoyloxymethyl-4-(R)—(N-benzoylcytosin-1-yl)-1,3-oxathiolane (15 g, 0.028 mol) was dissolved in a methanolic ammonia (approximately 2M) solution (250 mL). The initial slurry was stirred overnight. After overnight stirring, the resulting clear solution was filtered through celite, evaporated to dryness and slurried in acetone (100 mL). This yielded off-white powdery solid which was filtered and washed with acetone (2×25 mL), and dried to yield the product. 6.5 g (94%).

$^1$H NMR(DMSO): δ 7.8 (d, 1H), 7.0-7.2 (broad d, 2H), 6.3 (d, 1H), 5.7 (d, 1H), 5.3 (t, 1H) (OH peak—not always resolved), 5.1 (t, 1H), 4.4 (d, 1H), 3.9 (m, 1H), 3.7 (m, 2H), OH peak not resolved

Example 9

Synthesis of 2-(R)-hydroxymethyl-4-(R)-(cytosin-1-yl)-1,3-oxathiolane

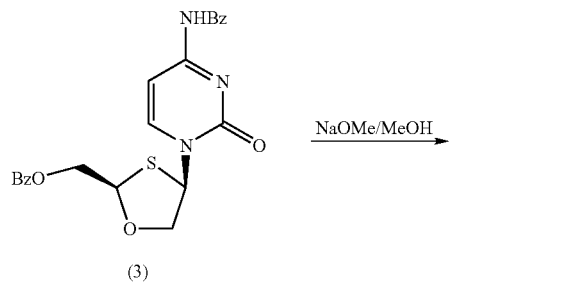

| Reagent | Molecular Weight | Equivalents | Moles | Amount |
|---|---|---|---|---|
| 2-(R)-benzoyloxy-methyl-4-(R)-(N-benzoylcytosin-1-yl)-1,3-oxathiolane | 437.4 | 1 | 0.007 | 3.3 g |
| NaOMe (prepared from Na and methanol) | 54 | 0.11 | 0.0008 | 0.43 g |
| Dichloromethane | | | | 8 mL |
| Methanol | | | | 10 mL |

Procedure:

2-(R)-benzoyloxymethyl-4-(R)—(N-benzoylcytosin-1-yl)-1,3-oxathiolane (3.3 g, 0.007 mol) was dissolved in a mixture of dichloromethane (8 mL) and methanol (10 mL) with heating. To this was added sodium methoxide (0.043 g, 0.0008 mol) in methanol (2 mL) and the mixture was stirred overnight. After overnight stirring, the mixture was evaporated and was chromatographed on a silica gel column (4×18 cm) eluting using a gradient of 20-50% methanol in Ethyl acetate. Combination and evaporation of the appropriate fractions yielded 1.5 g (88% yield) of the product (5) as an off white powder.

$^1$H NMR(DMSO): δ 7.8 (d, 1H), 7.0-7.2 (broad d, 2H), 6.3 (d, 1H), 5.7 (d,1 H), 5.1 (t, 1H), 4.4 (d, 1H), 3.9 (m, 1H), 3.7 (m, 2H), OH peak not resolved

Example 10

Synthesis of 2-(S)-hydroxymethyl-4-(S)-(cytosin-1-yl)-1,3-oxathiolane

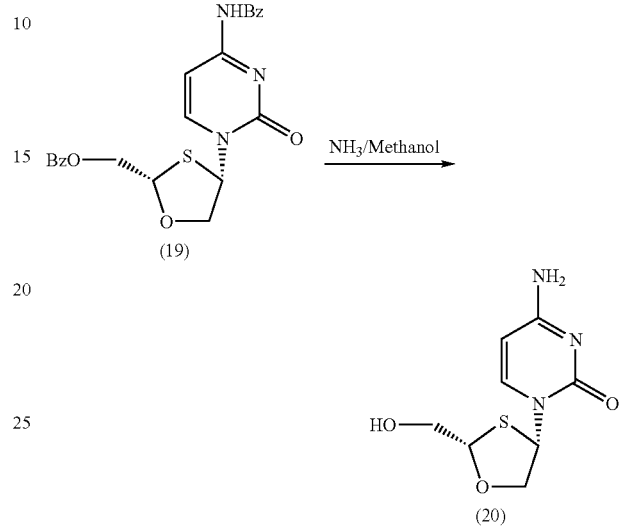

2-(S)-benzoyloxymethyl-4-(S)—(N-benzoylcytosin-1-yl)-1,3-oxathiolane (1.0 g, 0.0022 mol) was dissolved in a methanolic ammonia (approximately 2M) solution (20 mL). The initial slurry was stirred overnight. After overnight stirring, the resulting clear solution was evaporated to dryness and slurried in acetone (20 mL). This yielded off-white powdery solid which was filtered and washed with acetone (2×10 mL), and dried to yield the product. 0.47 g (88%).

$^1$H NMR(DMSO): δ 7.8 (d, 1H), 7.0-7.2 (broad d, 2H), 6.3 (d, 1H), 5.7 (d,1 H), 5.3 (t, 1H) (OH peak—not always resolved), 5.1 (t, 1H), 4.4 (d, 1H), 3.9 (m, 1H), 3.7 (m, 2H), OH peak not resolved

Example 11

Synthesis of 2-(R)-benzoyloxymethyl-4-(R)—(N-acetylcytosin-1-yl)-1,3-oxathiolane

Coupling of 2-(R)-benzoyloxymethyl-1,3-oxathiolane with N-acetyl cytosine

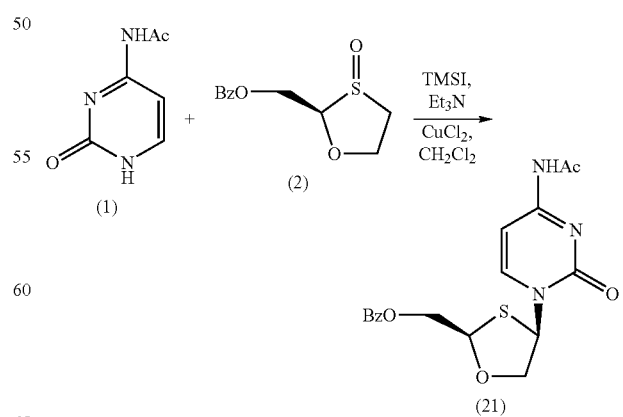

Ac = CH$_3$CO
Bz = C$_6$H$_5$CO 2-(R)-benzoyloxymethyl-1,3-oxathiolane (5.0 g, 0.021 mol) was dissolved in dichloromethane (100 mL) in a 500 mL 3-neck flask under nitrogen and to this triethylamine (6.08 mL, 0.044 mol) was added. The solution was cooled to −50° C. next and iodotrimethylsilane (9.22 mL, 0.065 mol) was added to this via a dropping funnel dropwise, at a rate, the internal temperature did not rise above −40° C. The resulting light yellow solution was stirred for 1 hour, while maintaining the temperature at −50° C. Next, to the reaction mixture, copper(II)chloride (0.28 g, 0.021 mol) was added followed by N-acetylcytosine (5.0 g, 0.021 mol). The resulting mixture was stirred at −50° C. for 15 minutes, allowed to warm to 0° C. and stirred at this temperature overnight. After overnight stirring, the reaction was stirred at room temperature for 1 hour, quenched with the addition of water (50 mL) immediately followed by 5% ammonia (100 mL). This was stirred well for 10 minutes, filtered through a celite plug (8×3 cm). The flask and the plug were washed with additional dichloromethane (100 mL, 2×50 mL). The combined, clear filtrates were poured into a separating funnel and the organic layer was separated out. The organic layer was then washed with 2% phosphoric acid (100 mL). The combined aqueous layers were re-extracted with dichloromethane (100 mL). The combined organic layers were dried with magnesium sulphate, filtered and evaporated to give a light yellow/light brown viscous oil 6.8 g (92% recovery).

NMR analysis of the crude gave the following data: Extent of the reaction (NMR estimated purity of the total coupled product): 73%; C/T ratio: 2.37:1; Amount of olefin by-product (with respect to the total coupled product): 8%

Example 12

Synthesis of 2-(R)-benzoyloxymethyl-4-(R)—(N-benzoyl-5-fluorocytosin-1-yl)-1,3-oxathiolane (a) Coupling of 2-(R,S)-benzoyloxymethyl-1,3-oxathiolane with N-benzoyl-5-fluorocytosine

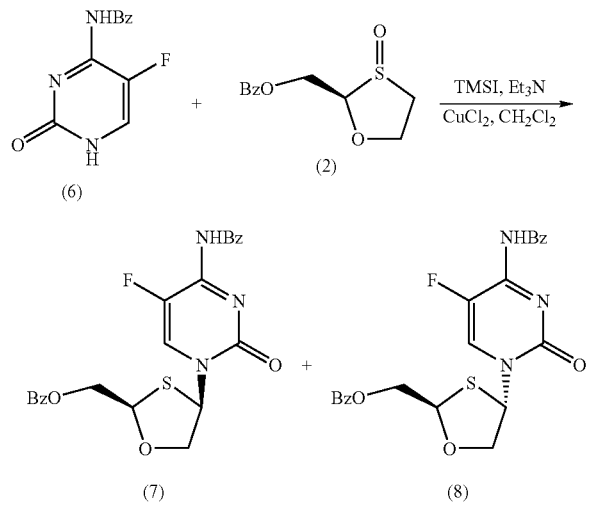

| Reagent | Molecular Weight | Equivalents | Moles | Amount |
| --- | --- | --- | --- | --- |
| 2-(R,S)-benzoyloxymethyl-1,3-oxathiolane | 240.3 | 1.0 | 0.040 | 9.6 g |
| N-benzoylcytosine | 215.1 | 1.0 | 0.040 | 9.3 g |
| Iodotrimethylsilane | 200.1 d = 1.406 | 3.1 | 0.124 | 24.9 g 17.7 mL |

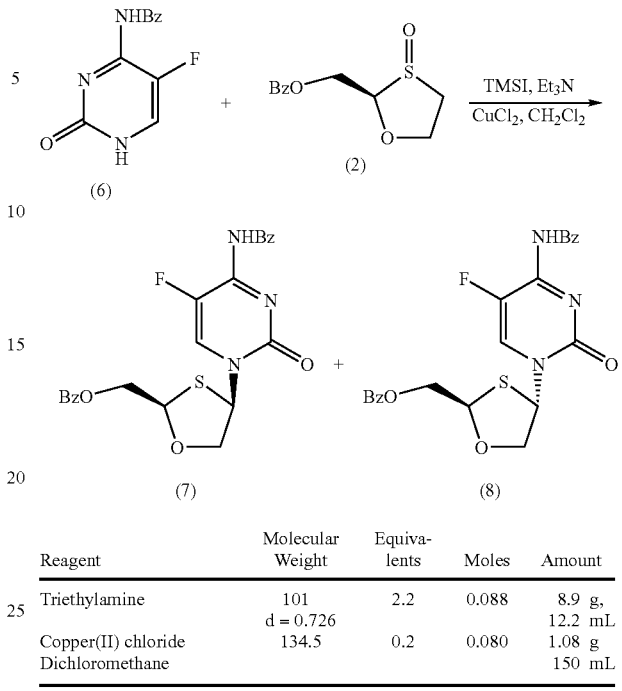

| Reagent | Molecular Weight | Equivalents | Moles | Amount |
| --- | --- | --- | --- | --- |
| Triethylamine | 101 d = 0.726 | 2.2 | 0.088 | 8.9 g, 12.2 mL |
| Copper(II) chloride | 134.5 | 0.2 | 0.080 | 1.08 g |
| Dichloromethane | | | | 150 mL |

Bz = C₆H₅CO

Procedure:

To a mixture of 2-(R)-benzoyloxymethyl-1,3-oxathiolane and 2-(S)-benzoyloxymethyl-1,3-oxathiolane (9.6 g, 0.040 mol) was dissolved in dichloromethane in a 500 mL 3-neck flask and this was cooled to −50° C. To this triethylamine (12.2 mL, 0.088 mol) was added and followed by iodotrimethylsilane (17.7 mL, 0.124 mol) via a dropping funnel, dropwise, at a rate so that the internal temperature was between −35° C. and −50° C. The resulting light yellow solution was stirred for 60 minutes while maintaining the temperature between −40° C. and −50° C. Next, to the reaction mixture, was added copper(II)chloride (1.3 g, 0.010 mol) and after 5 more minutes was added N-benzoyl-5-fluorocytosine (9.3 g, 0.040 mol). The resulting mixture was stirred at −50° C. for 15 minutes and then was allowed to warm to 0° C. over 1 hour. The reaction mixture was stirred at this temperature overnight. After overnight stirring, the reaction was stirred at room temperature for 1 hour, cooled again in ice, quenched with the addition of saturated sodium bicarbonate (75 mL). This was stirred for 5 minutes, diluted with dichloromethane (50 mL) and filtered through a celite plug. The plug was washed with additional dichloromethane (2×50 mL) and the combined filtrates were poured into a separating funnel. The organic layer was separated, washed 5% ammonia (100 mL), 2% phosphoric acid (2×60 mL) and again with 5% ammonia (100 mL). The combined aqueous layers were re-extracted with dichloromethane (100 mL). The combined organic layers were dried with magnesium sulphate, filtered and evaporated to give a light yellow/brown thick oil 14.6 g (80% recovery). This crude mixture consisted of cis (R,R and S,S) and trans (S,R and R,S) combined coupled product at 55% purity (NMR) and with a cis:trans isomer ratio 2.65:1 (NMR).

(b) Recrystallization of the crude 2-(R,S)-benzoyloxymethyl-4-(R,S)—(N-benzoyl-5-fluorocytosin-1-yl)-1,3-oxathiolane to give pure 2-(R)-benzoyloxymethyl-4-(R)—(N-benzoyl-5-fluorocytosin-1-yl)-1,3-oxathiolane

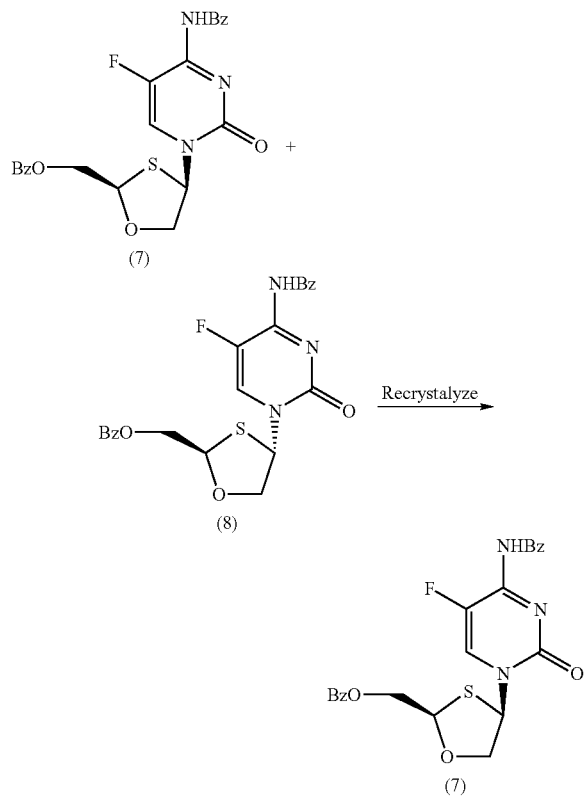

To the crude (R)-benzoyloxymethyl-4-(R,S)—(N-benzoyl-5-fluorocytosin-1-yl)-1,3-oxathiolane (14.6 g) in a 500 mL round bottom flask, was added 10 times (by volume) methanol (146 mL) and the mixture was refluxed till a clear solution could be seen. This was hot filtered and then allowed to cool to room temperature gradually and was left standing overnight. The resulting crystallized product was filtered, followed by washing with methanol (2×100 mL) and drying under vacuum. The resulting slightly coloured powdery crystalline solid on analysing with NMR showed that it is >98% the cis isomer. Isolated yield, 3.5 g (19% yield for the cis isomer(7)).

$^1$H NMR(DMSO): δ 7.95 (m, 3H), 7.75 (m, 2H), 7.6 (m, 2H), 7.6-7.4 (m, 4H), 6.22 (dd, 1H), 5.43 (t, 1H), 4.7 (m, 2H), 4.55 (d, 1H), 3.95 (dd, 1H)

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

REFERENCES

1. Belleau et. al., *Bioorg. Med. Chem. Lett.* (1993) Vol. 3, No. 8, 1723-1728.
2. Taylor et. al., *Antiviral Chem. Chemother.* (2000) Vol. 11, No. 4, 291-301.
3. Stoddart et. al., *Antimicrob. Agenst Chemother.* (2000) Vol, 44, No. 3, 783-786.
4. Mansour et. al., *J. Med. Chem.*, (1995) Vol. 38, No. 1: 1-4.
5. *Nucleosides and Nucleotides* (1995) 14(3-5): 627-735.
6. Caputo et. al. *Eur. J. Org. Chem.* (1999) Vol. 6: 1455-1458.
7. J. Jacques, A. Collet & S. H. Wilen "Enantiomers, Racemates and Resolutions" by (John Wiley & Sons, 1981).
8. Storer et. al., *Nucleosides & Nucleotides* (1993) 12(2): 225-236.
9. Lorenz, H., et. al., *Journal of the University of Chemical Technology and Metallurgy* (2007) 42(1): 5-16.
10. Greene, T. W. and Wuts, P. G. M "Protective groups in organic synthesis" (3$^{rd}$ Edition) 1999 John Wiley & Sons Inc.

The invention claimed is:

1. A process for producing a compound of general formula (II) comprising the steps of:
   (a) forming a 2-substituted 4-substituted 1,3-oxathiolane of general formula (II) and (III):

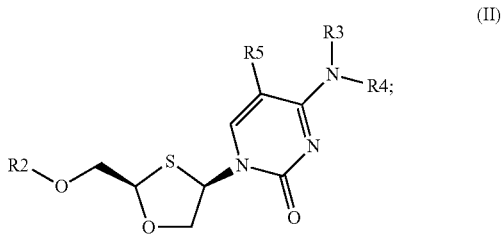

-continued

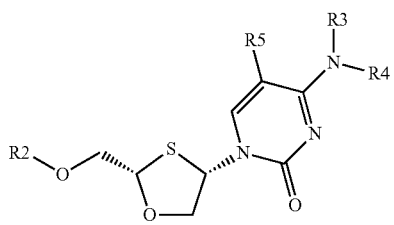

wherein

R2 is C(O)phenyl;

R3 and R4 are each individually selected from H or benzoyl, provided that when R3 is H, R4 is not H and when R4 is H, R3 is not H; and R5 is H, Br, Cl, F, I or CF$_3$; and (b) selective recrystallisation of the compound of general formula (II) from a solvent wherein the solvent is C$_{1-6}$alcohol or mixtures of C$_{1-6}$alcohols.

2. The process of claim 1, wherein (a) comprises:

reacting a base of general formula (IV) with a 1,3-oxathiolane of general formula (V) to produce a compound of general formula (II) and (III):

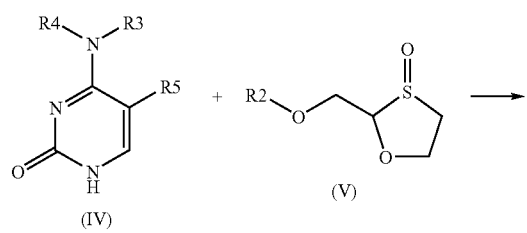

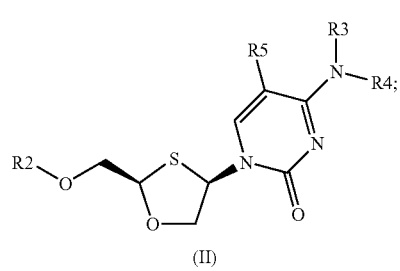

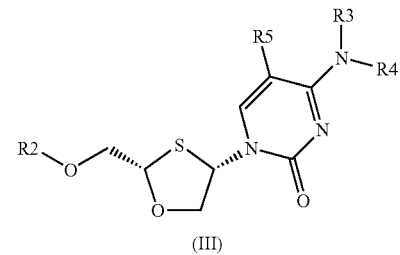

wherein the 1,3-oxathiolane of general formula (V) is the (R)-enantiomer in at least 60% ee.

3. A process for producing a compound of general formula (VI) comprising the steps of:

(a) forming a 2-substituted 4-substituted 1,3-oxathiolane of general formula (II) and (III):

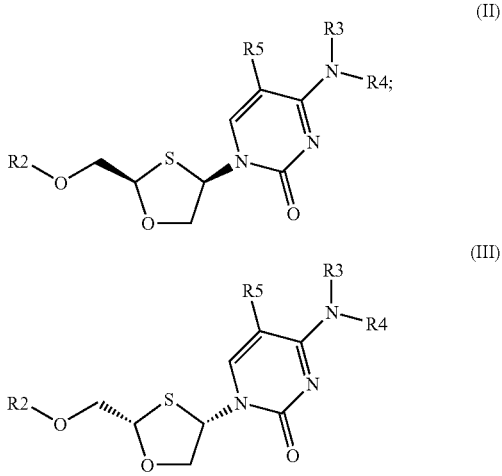

wherein

R2 is C(O)phenyl;

R3 and R4 are each individually selected from H or benzoyl, provided that when R3 is H, R4 is not H and when R4 is H, R3 is not H; and R5 is H, Br, Cl, F, I or CF$_3$;

(b) selective recrystallisation of the compound of general formula (II) from a solvent wherein the solvent is C$_{1-6}$alcohol or mixtures of C$_{1-6}$alcohols; and (c) deprotecting the compound of general formula (II) to produce a compound of general formula (VI):

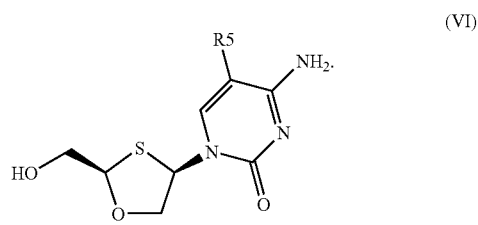

4. The process of claim 3, wherein (a) comprises:

reacting a base of general formula (IV) with a 1,3-oxathiolane of general formula (V) to produce a compound of general formula (II) and (III):

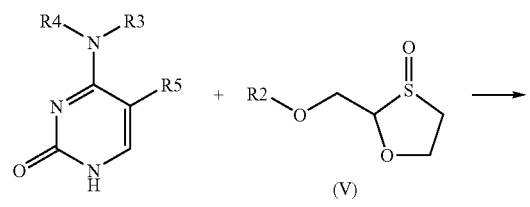

-continued

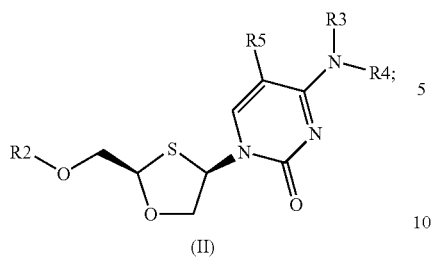

(II)

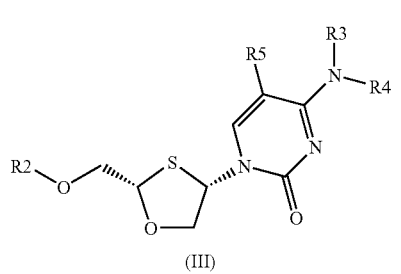

(III)

wherein the 1,3-oxathiolane of general formula (V) is the (R)-enantiomer in at least 60% ee.

5. The process according to claim 1, wherein R5 is H or F.

6. A process for producing a compound of general formula (VI) or (VII) from a compound of general formula (VIII) or (IX) respectively, comprising the step of:

(a) deprotecting a compound of general formula (VIII) or (IX) to produce a compound of general formula (VI) or (VII) respectively:

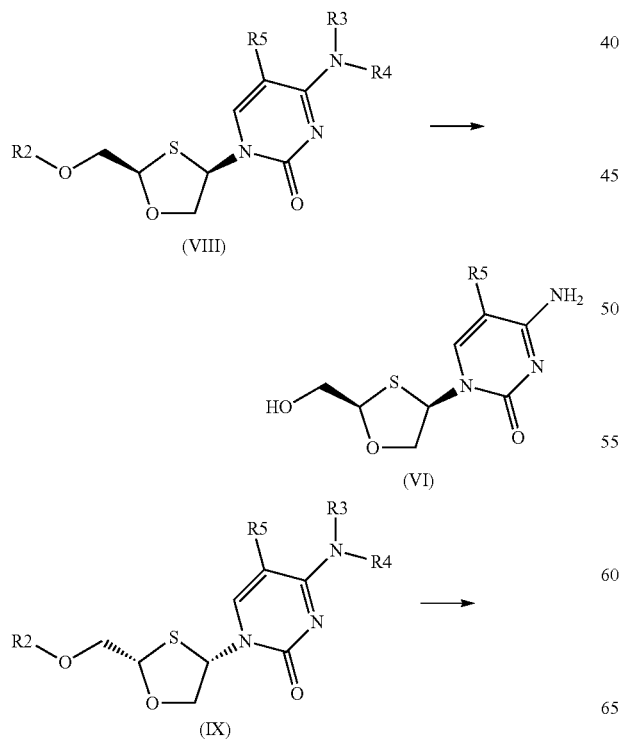

-continued

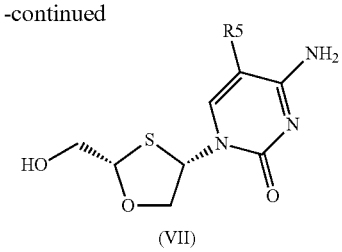

(VII)

wherein
R2 is C(O)benzyl;
R3 and R4 are each individually selected from H or benzoyl, provided that when R3 is H, R4 is not H and when R4 is H, R3 is not H; and
R5 is H, Br, Cl, F, I or $CF_3$.

7. The process according to claim 6, wherein R5 is H or F.

8. A process for producing a compound of general formula (II) comprising the steps of:

(a) reacting a silylated base of general formula (X) with a 1,3-oxathiolane of general formula (V) to produce a compound of general formula (II) and (III):

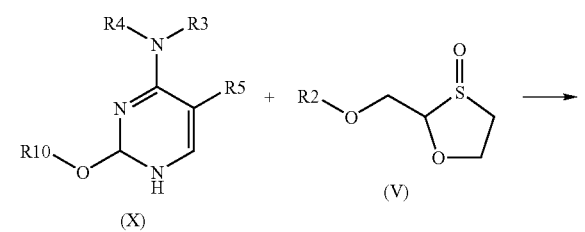

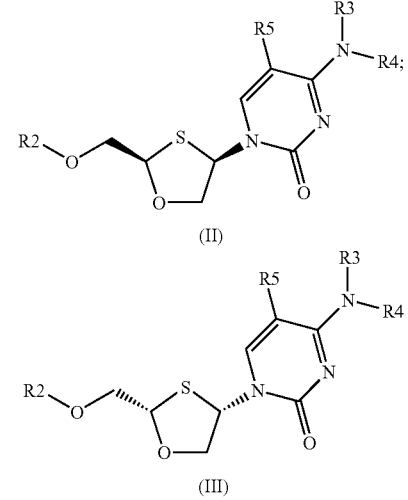

wherein
R2 is C(O)phenyl;
R3 and R4 are each individually selected from H or benzoyl, provided that when R3 is H, R4 is not H and when R4 is H, R3 is not H; and
R5 is H, Br, Cl, F, I or $CF_3$; and
R10 is a silyl protecting group of general formula SiR7R8R9 wherein R7, R8 and R9 are each independently selected from $C_{1-6}$alkyl, aryl or $C_{1-6}$alkylaryl; and
wherein the 1,3-oxathiolane of general formula (V) is the (R)-enantiomer in at least 60% ee; and (b) selective recrystallisation of the compound of general formula (II) from a solvent wherein the solvent is $C_{1-6}$alcohol or mixtures of $C_{1-6}$alcohols.

9. A process for producing a compound of general formula (VI) comprising the steps of:
   (a) reacting a silylated base of general formula (X) with a 1,3-oxathiolane of general formula (V) to produce a compound of general formula (II) and (III):

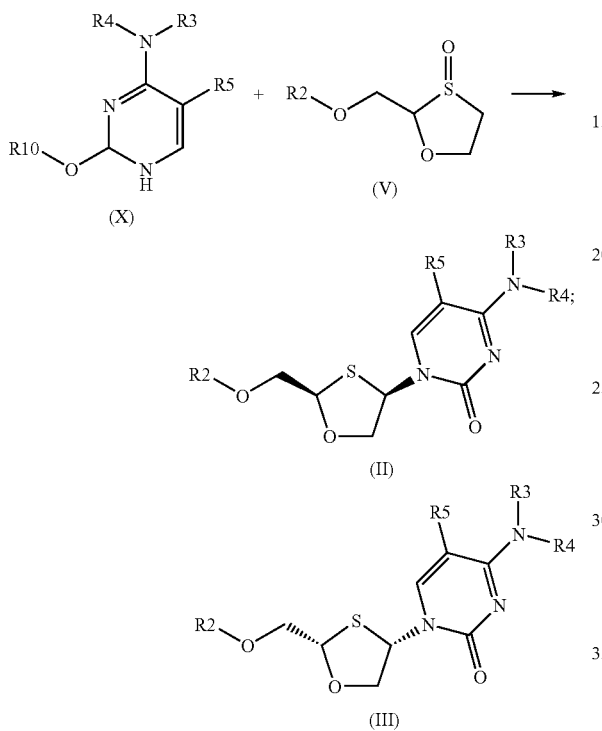

wherein
R2 is C(O)phenyl;
R3 and R4 are each individually selected from H or benzoyl, provided that when R3 is H, R4 is not H and when R4 is H, R3 is not H;
R5 is H, Br, Cl, F, I or $CF_3$; and
R10 is a silyl protecting group of general formula SiR7R8R9 wherein R7, R8 and R9 are each independently selected from $C_{1-6}$alkyl, aryl or $C_{1-6}$alkylaryl;
wherein the 1,3-oxathiolane of general formula (V) is the (R)-enantiomer in at least 60% ee;
   (b) selective recrystallisation of the compound of general formula (II) from a solvent wherein the solvent is $C_{1-6}$alcohol or mixtures of $C_{1-6}$alcohols; and
   (c) deprotecting the compound of general formula (II) to produce a compound of general formula (VI):

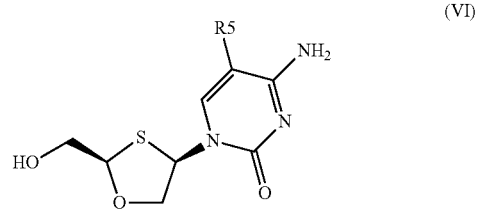

10. A process for separating a compound of general formula (II) from a compound of general formula (III) comprising the steps of:
    (a) providing a mixture of 2-substituted 4-substituted 1,3-oxathiolanes of general formula (II) and (III):

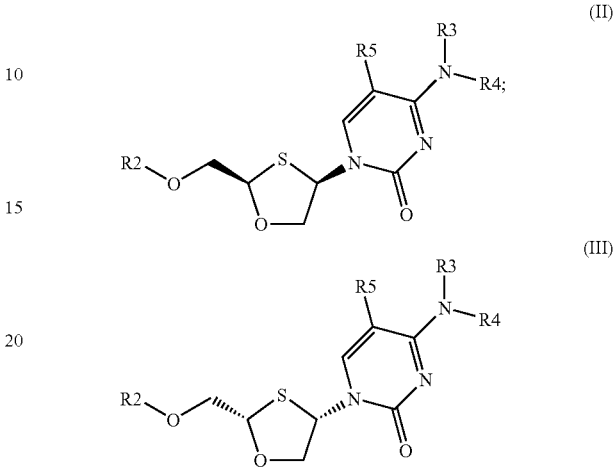

wherein
R2 is C(O)phenyl;
R3 and R4 are each individually selected from H or benzoyl, provided that when R3 is H, R4 is not H and when R4 is H, R3 is not H; and
R5 is H, Br, Cl, F, I or $CF_3$; and
    (b) separating the compound of general formula (II) from the compound of general formula (III) by selective recrystallisation of the compound of general formula (II) from a solvent wherein the solvent is $C_{1-6}$alcohol or mixtures of $C_{1-6}$alcohols.

11. The process according to claim 2, wherein 1,3-oxathiolane of general formula (V) is greater than 95% ee.

12. The process according to claim 11 wherein the 1,3-oxathiolane of general formula (V) is greater than 99% ee.

13. The process according to claim 1, wherein the solvent is $C_{1-6}$alcohol selected from the group consisting of methanol (MeOH), ethanol (EtOH), propanol and butanol.

14. The process according to claim 13 wherein the $C_{1-6}$alcohol is methanol.

15. The process according to claim 1, wherein the solvent is a mixture of $C_{1-6}$alcohols comprising MeOH.

16. The process according to claim 15 wherein the mixture of $C_{1-6}$alcohols is in the ratio of 90:10 MeOH:$C_{2-6}$alcohol.

17. The process according to claim 15 wherein the ratio is 95:5 MeOH:$C_{2-6}$alcohol.

18. The process according to claim 13, wherein the solvent contains no more than about 5% water.

19. The process according to claim 1, wherein the selective recrystallisation step (b) is repeated at least once.

20. The process according to claim 1, wherein the selective recrystallisation step (b) is an entrainment or a cyclic entrainment process.

21. The process according to claim 20 wherein the entrainment or cyclic entrainment process comprises seeding with an R,R-enantiomer.

22. The process according to claim 21 wherein the seeding is performed at a temperature less than or about 55° C.

23. The process according to claim 1, wherein the 2-substituted 4-substituted 1,3-oxathiolane of general formula (II) or general formula (III) produced or formed in step (a) is in the form of a conglomerate.

24. The process according to claim 1, wherein the 2-substituted 4-substituted 1,3-oxathiolane of general formula (II) or general formula (III) produced or formed does not comprise any detectable amount of an undesired isomer.

25. A compound of general formula (VIII) or (IX):

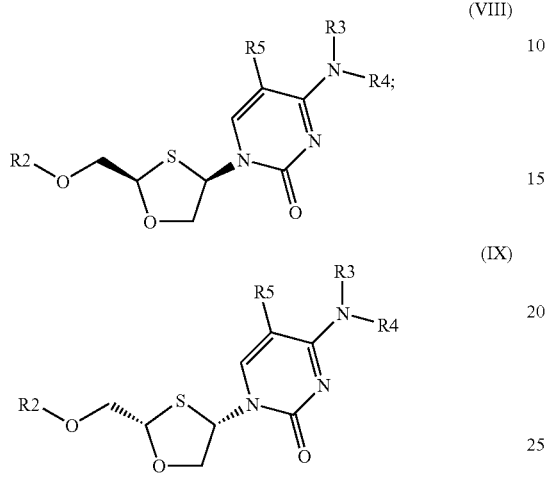

wherein

R2 is C(O)phenyl;

R3 and R4 are each individually selected from H or benzoyl, provided that when R3 is H, R4 is not H and when R4 is H, R3 is not H; and R5 is H, Br, Cl, F, I or CF$_3$.

26. The compound according to claim 25, wherein R5 is H or F.

27. The compound of claim 25, wherein the compound is selected from the group of compounds consisting of:

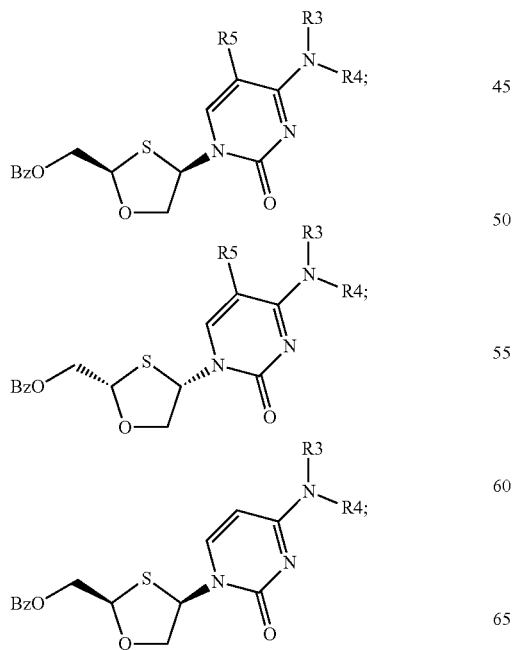

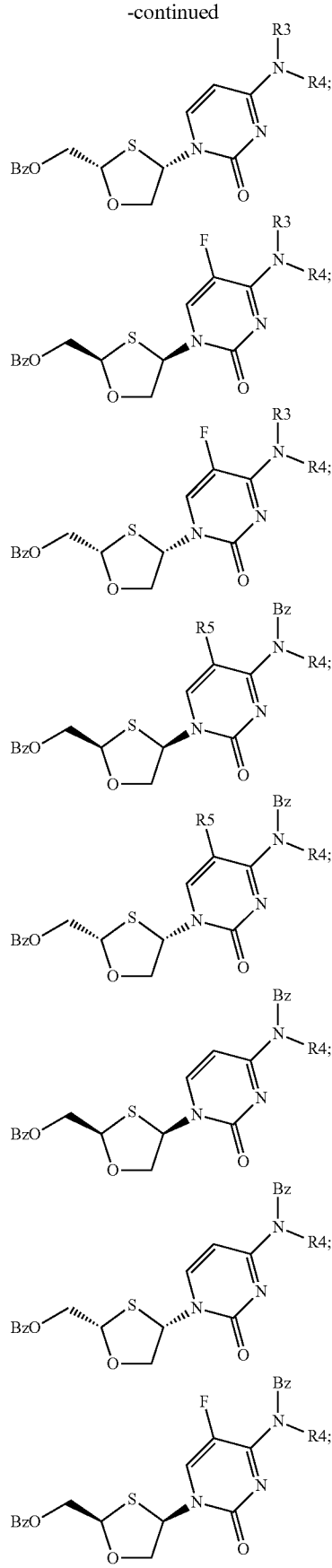

-continued

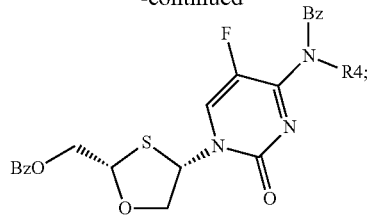

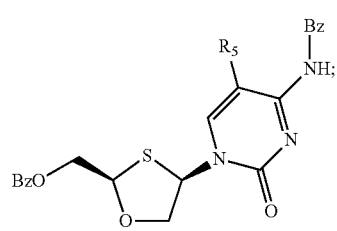

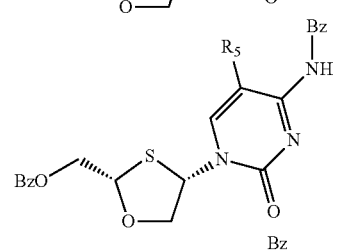

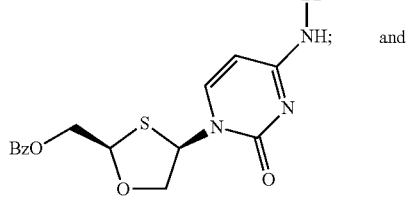 and

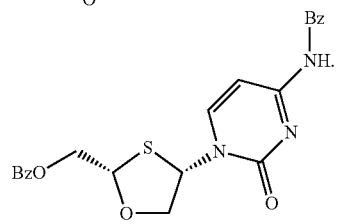

28. A compound of general formula (VIII) or (IX):

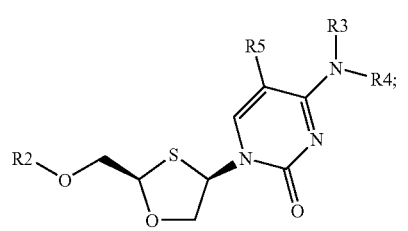
(VIII)

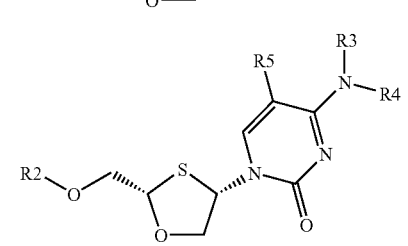
(IX)

wherein

R2 is C(O)phenyl;

R3 and R4 are each individually selected from H or benzoyl, provided that when R3 is H, R4 is not H and when R4 is H, R3 is not H; and R5 is H, Br, Cl, F, I or $CF_3$, wherein the compound is amenable to selective recrystallization from a solvent.

29. The compound of claim 28, wherein the solvent is $C_{1-6}$alcohol or mixtures of $C_{1-6}$alcohols.

30. The compound of claim 28, wherein R5 is H or F.

31. The compound of claim 28, wherein the compound is selected from the group of compounds consisting of:

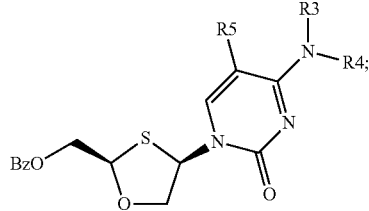

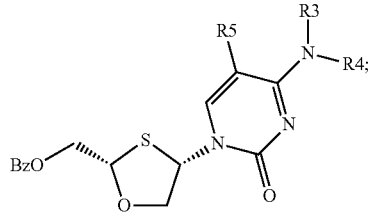

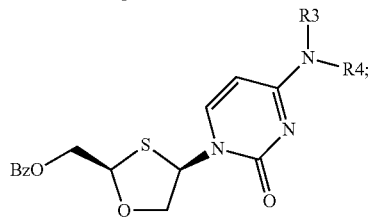

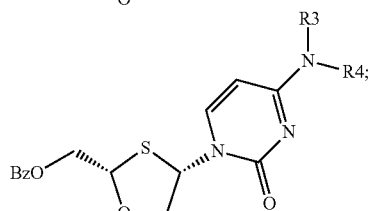

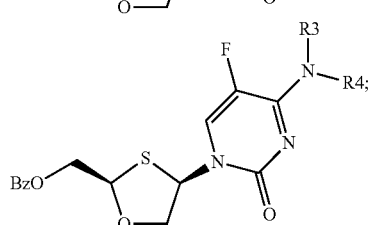

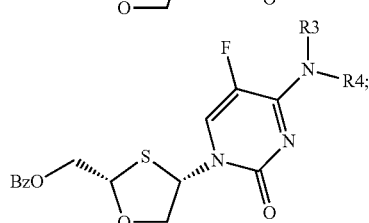

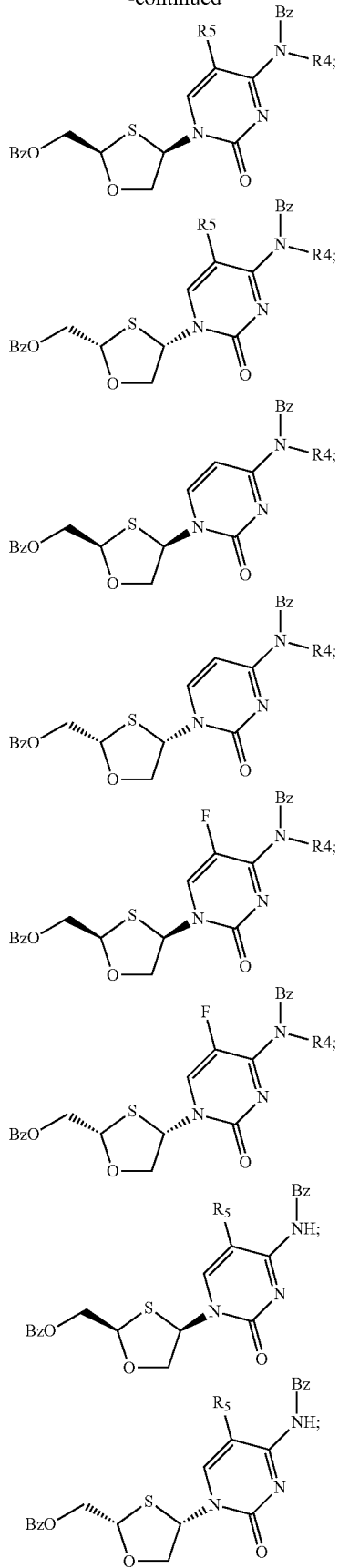

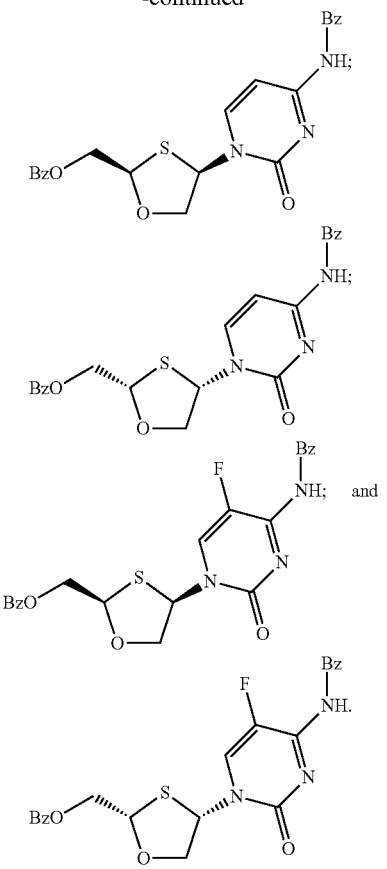

32. The compound of claim 29, wherein the solvent is $C_{1-6}$alcohol selected from the group consisting of methanol (MeOH), ethanol (EtOH), propanol and butanol.

33. The compound of claim 32 wherein the $C_{1-6}$alcohol is methanol.

34. The compound of claim 29, wherein the solvent is a mixture of $C_{1-6}$alcohols comprising MeOH.

35. The compound of claim 34 wherein the mixture of $C_{1-6}$alcohols is in the ratio of 90:10 MeOH:$C_{2-6}$alcohol.

36. The compound of claim 34 wherein the ratio is 95:5 MeOH:$C_{2-6}$alcohol.

37. The compound of claim 29, wherein the solvent contains no more than about 5% water.

38. The compound of claim 28, wherein the selective recrystallisation is an entrainment or a cyclic entrainment process.

39. The compound of claim 38 wherein the entrainment or cyclic entrainment process comprises seeding with an R,R-enantiomer.

40. The compound of claim 39 wherein the seeding is performed at a temperature less than or about 55° C.

41. The compound of claim 28, wherein the compound is in the form of a conglomerate.

42. The compound of claim 28, wherein the compound does not comprise any detectable amount of an undesired isomer.

* * * * *